(12) United States Patent
Raso

(10) Patent No.: US 7,749,966 B2
(45) Date of Patent: Jul. 6, 2010

(54) IMMUNOLOGICAL MODULATION OF INSULIN-LIKE GROWTH FACTOR 1 FOR CANCER PREVENTION/TREATMENT AND PROLONGING LONGEVITY

(75) Inventor: Victor Raso, Brighton, MA (US)

(73) Assignee: Boston Biomedical Research Institute, Watertown, MA (US)

(*) Notice: Subject to any disclaimer, the term of this patent is extended or adjusted under 35 U.S.C. 154(b) by 28 days.

(21) Appl. No.: 12/004,589

(22) Filed: Dec. 20, 2007

(65) Prior Publication Data

US 2008/0187536 A1 Aug. 7, 2008

Related U.S. Application Data

(60) Provisional application No. 60/876,342, filed on Dec. 21, 2006.

(51) Int. Cl.
A61K 38/00 (2006.01)
C07K 5/00 (2006.01)
(52) U.S. Cl. ............................ 514/13; 514/14; 530/326
(58) Field of Classification Search ........................ None
See application file for complete search history.

(56) References Cited

U.S. PATENT DOCUMENTS

| 6,582,945 | B1 | 6/2003 | Raso |
| 6,872,554 | B2 | 3/2005 | Raso |
| 6,932,971 | B2 | 8/2005 | Bachmann |

FOREIGN PATENT DOCUMENTS

| WO | 96/02270 | * | 2/1996 |
| WO | 2006/047214 | * | 4/2006 |

OTHER PUBLICATIONS

Essell (J. NIH Res. 1995 7:46).*
Spitler (Cancer Biotherapy, 1995, 10:1-3.*
Boon (Adv. Can. Res. 1992 58:177-210).*
Chua et al. Comparison of lipopeptide-based immunocontraceptive vaccines containing different lipid groups. Vaccine (Available online Jul. 31, 2006), 25(1):92-101; p. 92, abstract; p. 93, para 5 and 8; p. 99, para 4; p. 100, para 6.
Adams et al. Structure and function of the type 1 insulin-like growth factor receptor. Cellular and Molecular Life Science, Jul. 2000, 57(7):1050-1093; p. 1071, para 3; p. 1080, para 3 and 5.
JM Chan et al., J Natl Cancer Inst 94:1099-1106 (2002).
JM Chan et al., Science 279: 563-566 (1998).
Dunn, S.E., et al. Cancer Res 57:4667-4672 (1997).
Kari, F.W., et al. J Nutr Health Aging 3:92-101 (1999).
Kenyon, C. Cell 120:449-460 (2005).
Holzenberger, M., et al. Nature 421:182-187 (2003).
Vijg, J., and Y. Suh. Annu Rev Med 56:193-212 (2005).
Butler, R.N., et al. J Gerontol A Biol Sci Med Sci 58:581-584 (2003).
Dumble, M., et al. Ann N Y Acad Sci 1019:171-177 (2004).
Maier, B., et al. Genes Dev 18:306-319 (2004).
Hursting, S.D., et al. J Nutr 134:2482S-2486S (2004).
Bartke, A., et al. Nature 414:412 (2001).
Schurmann, A., et al. Experientia 52:55-59 (1996).
Spencer, G.S., et al. Endocrinology 128:2103-2109 (1991).
Koea, J.B., et al. J Endocrinol 135:279-284 (1992).
Stewart, C.E., et al. Endocrinology 133:1462-1465 (1993).
Kerr, D.E., et al. J Endocrinol 124:403-415 (1990).
Cohen, B.D., et al. Clin Cancer Res 11:2063-2073 (2005).
Araki, K., et al. Intl J Cancer 118:2602-2608 (2006).
Goya, M., et al. Cancer Res 64:6252-6258 (2004).
Miyamoto, S., et al. Clin Cancer Res 11:3494-3502 (2005).
Bachmann, M.F., et al. Science 262:1448-1451 (1993).
Chackerian, B., et al. J Immunol 169:6120-6126 (2002).
Cielens, I., et al. FEBS Lett 482:261-264 (2000).
Kozlovska, T.M., et al. Gene 137:133-137 (1993).
Kozlovska, T.M., et al. Intervirology 39:9-15 (1996).
Denley, A., et al. Cytokine Growth Factor Rev 16:421-439 (2005).
Spohn, G., et al. J Immunol 175:6211-6218 (2005).
Hu, JG, et al. Chem Pharm Bull (Tokyo) 37: 3042-3046 (1989).
Yakar, S., et al., Proc Natl Acad Sci U S A 96:7324-7329 (1999).
Golmohammadi, R., et al. Structure 4:543-554 (1996).
Miller, R.A., and N. L. Nadon, et al. J Gerontol A Biol Sci Med Sci 55:B117-123 (2000).
Nadon, N. L. et al., J Gerontol A Biol Sci Med Sci 61:813-815 (2006).
Nadon, N. L., et al. Aging cell 5:9-15 (2006).
Warner, H.R., et al. Mech Ageing Dev 155:199-207 (2000).
Siddals, K.W., et al. J Biol Chem 279:38353-38359 (2004).
Ballard, F.J., et al. Biochem J 233:223-230 (1986).
Zheng, W.H., and R. Quirion, et al. BMC Neurosci 7:51 (2006).
Majeed, N., et al. Oncogene 24:4736-4740 (2005).
Hursting, S.D., et al. Cancer Res 57:2843-2846 (1997).
DiGiovanni, J., et al. Proc Natl Acad Sci U S A 97:3455-3460 (2000).
Husler, M.R., et al. Transgenic Res 7:253-263 (1998).
Lupu, F., et al. Dev Biol 229:141-162 (2001).
Pell, J., et al. Endochrinology, 141:741-751 (2000).
Meeker, T.C., et al. Blood, 65:1349-1363.

* cited by examiner

Primary Examiner—Sheela J Huff
(74) Attorney, Agent, or Firm—Pierce Atwood LLP; Kevin M. Farrell; David J. Wilson

(57) ABSTRACT

Provided is a simple and safe immunization procedure to reduce cancer incidence and increase longevity by modulating IGF-1 levels in the body. Described are cancer preventive vaccines and methods that elicit circulating antibodies specific to insulin-like growth factor 1 (IGF-1) in the body. Many cancers will be less likely to occur and spread in the absence or reduced levels of the stimulatory signals provided by IGF-1. Longevity also can be extended by immunologically lowering the level of bioavailable IGF-1 in adult animals. This prolongation of lifespan resulting from lower IGF-1 levels is produced independently of the inhibitory effects on carcinogenesis. However, the two IGF-1-mediated processes are linked mechanistically. Methods of active and passive immunization to suppress IGF-1 activity are included. Also described are methods for increasing longevity or reducing one or more symptoms of aging in a warm-blooded animal comprising administering anti-IGF-1 antibodies such that IGF-1 is inactivated or suppressed or administering IGF-1 antigen such that the animal produces endogenous antibodies to IGF-1.

8 Claims, 8 Drawing Sheets

```
GPETLCGAELVDALQFVCGDRGFYFNKPTGYGSSSRRAPQTGIVDECCFRSCDLRRLEMYCAPLKPAKSA
1           10         20         30         40         50         60         70
GPETLCGAELVDALQFVCGDRGFYFNKPTGYGSSSRRAPQTGIVDECCFRSCDLRRLEMYCAPLKPAKSA
1           10         20         30         40         50         60         70
GPETLCGAELVDALQFVCGPRGFYFNKPTGYGSSIRRAPQTGIVDECCFRSCDLRRLEMYCAPLKPTKAA
1           10         20         30         40         50         60         70
                              ↑                ↑                          ↑↑
```

Figure 1

GPETLCGAELVDALFVKLIPNASLIENCTKAEL            KLIPNASLIENCTKAELKTGYGSSSRRAPQTG
(1-16)              S                                            S                (29-42)
                    S-Pam3Cys                                    S-Pam3Cys

KLIPNASLIENCTKAELKRLEMYCAPLKPAKSA            GFYFNKPTGYGSSSKLIPNASLIENCTKAEL
                 S                (56-70)    (22-35)            S
                 S-Pam3Cys                                      S-
Pam3Cys

FIG. 6

IMMUNOLOGICAL MODULATION OF INSULIN-LIKE GROWTH FACTOR 1 FOR CANCER PREVENTION/TREATMENT AND PROLONGING LONGEVITY

This application claims priority to U.S. Provisional Application No. 60/876,342 filed on Dec. 21, 2006, which is incorporated herein by reference.

BACKGROUND

IGF-1 is a single chain polypeptide consisting of 70 amino-acid residues with three disulfide bridges. It may exert physiological effects via endocrine, autocrine, or paracrine pathways. IGF-1 is normally present in the blood and is usually complexed with binding proteins. The availability of IGF-1 in the bloodstream is regulated by at least six of these binding proteins. Some binding proteins inhibit IGF-1 activity while others increase it. Some of the binding proteins protect IGF-1 and greatly extend its serum half-life. Normally IGF-1 exits the circulation by crossing the endothelium to reach its target tissues and interact with their cell surface receptors. IGF-1 is the principal hormonal mediator of statural growth during childhood.

This small polypeptide hormone is also a known mitogen and plays a significant role in embryogenesis and early growth, carcinogenesis, hypertrophy and has anti-apoptotic activities. The IGF-1 receptor, which is a mediator of IGF-1's intracellular proliferative signaling, is over-expressed in many cancer cells. Epidemiological studies have linked high IGF-1 levels in the blood to several cancers including colorectal, prostate, uterine, bladder, ovarian and breast cancer. The Physicians' Health Study, for example, has indicated a strong association between circulating IGF-1 levels and the subsequent occurrence of prostate cancer (J M Chan, et al., J Natl Cancer Inst 94:1099-106 (2002); J M Chan, et al., Science 279: 451-566 (1998).

IGF-1 has at least two effects on cancer cells that lead to their uncontrolled proliferation. IGF-1, via multiple cellular signaling pathways, stimulates the synthesis of both DNA and protein. Moreover, IGF-1 signaling simultaneously inhibits apoptosis, thereby increasing cancer cell survival. In combination, these two effects can have a profound influence on carcinogenesis.

Higher cell proliferation rates increase the chance that a genetically damaged cell will divide to reach a critical mass and/or undergo a second transforming genetic mutation. Suppression of apoptosis aggravates the situation since this natural screening process can no longer eliminate damaged cells. If accumulative cellular damage precedes carcinogenesis, as the age relatedness of cancer would suggest, then minor alterations early in its progression could produce major consequences in the final outcome. Additionally, it is thought that IGF-1, as a result of its direct functions, may play a role in determining the longevity of an organism. In this regard, the longevity field provides research studies that indicate reduced IGF-1 signaling may be important in lifespan extension.

Thus, what is needed is a simple and method of increasing longevity and preventing cancer development and recurrence or growth by selectively modulating IGF-1 levels in the body.

SUMMARY OF THE INVENTION

Provided herein is a simple, safe, and effective vaccination procedure to reduce cancer incidence and increase longevity by modulating IGF-1 levels in the body. IGF-1 is a peptide normally circulating in the blood and responsible for statural growth during childhood. It has also been implicated in carcinogenesis and is known to play a role in determining lifespan.

The instant invention represents a particularly innovative form of cancer preventive and/or reduction therapy and a particularly innovative form of intervention to extend longevity. It takes advantage of the immune response in an unanticipated, new manner. Instead of fighting off a foreign pathogen, the IGF-1 vaccine will be used to regulate the bioavailable level of this natural growth factor and its stimulatory action in the body. This cancer preventive and lifespan extending invention makes use of the exquisite specificity of antibody-antigen interactions to selectively bind and functionally neutralize IGF-1. Emerging pre-cancer cells that are dependent on IGF-1 for proliferation and survival will thereby be curtailed early on, before they multiply, develop into a fully transformed clone, and spread. Once actively immunized, patients will continuously synthesize their own antibodies. Daily ingestion or injection is not required to maintain therapeutically active levels of antibody in the body.

Through passive immunization, anti-IGF-1 antibodies can be administered to an adult patient as a cancer preventative, cancer therapeutic, or to increase lifespan. The antibodies selectively bind and neutralize IGF-1, thereby interfering with IGF-1's its ability to bind its receptor and activate its signaling pathway. Anti-IGF-1 antibodies can also be elicited via active immunization with several different IGF-1 antigens. An animal vaccinated with the IGF-1 peptide, modified versions thereof, its analogs, or immunogenic fragments thereof can produce endogenous antibodies to IGF-1 continuously. Antibody titer in the vaccinated animal can be monitored and periodic booster injections given as necessary. Because antibodies are natural products, the adverse side effects that often accompany foreign substances are precluded. Patients treated with anti-IGF-1 antibodies or treated to produce anti-IGF-1 antibodies will have their IGF-1 signaling pathways disrupted. As a result of the IGF-1 hormone being sequestered by antibodies, the patients should live longer and/or experience fewer and delayed cancer occurrences.

BRIEF DESCRIPTION OF THE DRAWINGS

FIG. 1 shows the amino acid sequence of Human IGF-1 (SEQ ID NOS 1 and 2, respectively, in order of appearance) and Mouse IGF-1 (SEQ ID NO: 3); Target epitopes in Bold; sequences differ at ↑.

FIG. 6 shows self-adjuvanting IGF-1 Lipopeptide Vaccines: LPV-$IGF_{1-16}$, LPV-$IGF_{22-35}$, LPV-$IGF_{29-42}$ and LPV-$IGF_{56-70}$, IGF-1 Epitope (underline), Helper T Cell Epitope (double underline), Pam3Cys is the Lipid Moiety.

DETAILED DESCRIPTION OF THE INVENTION

Figure 2:
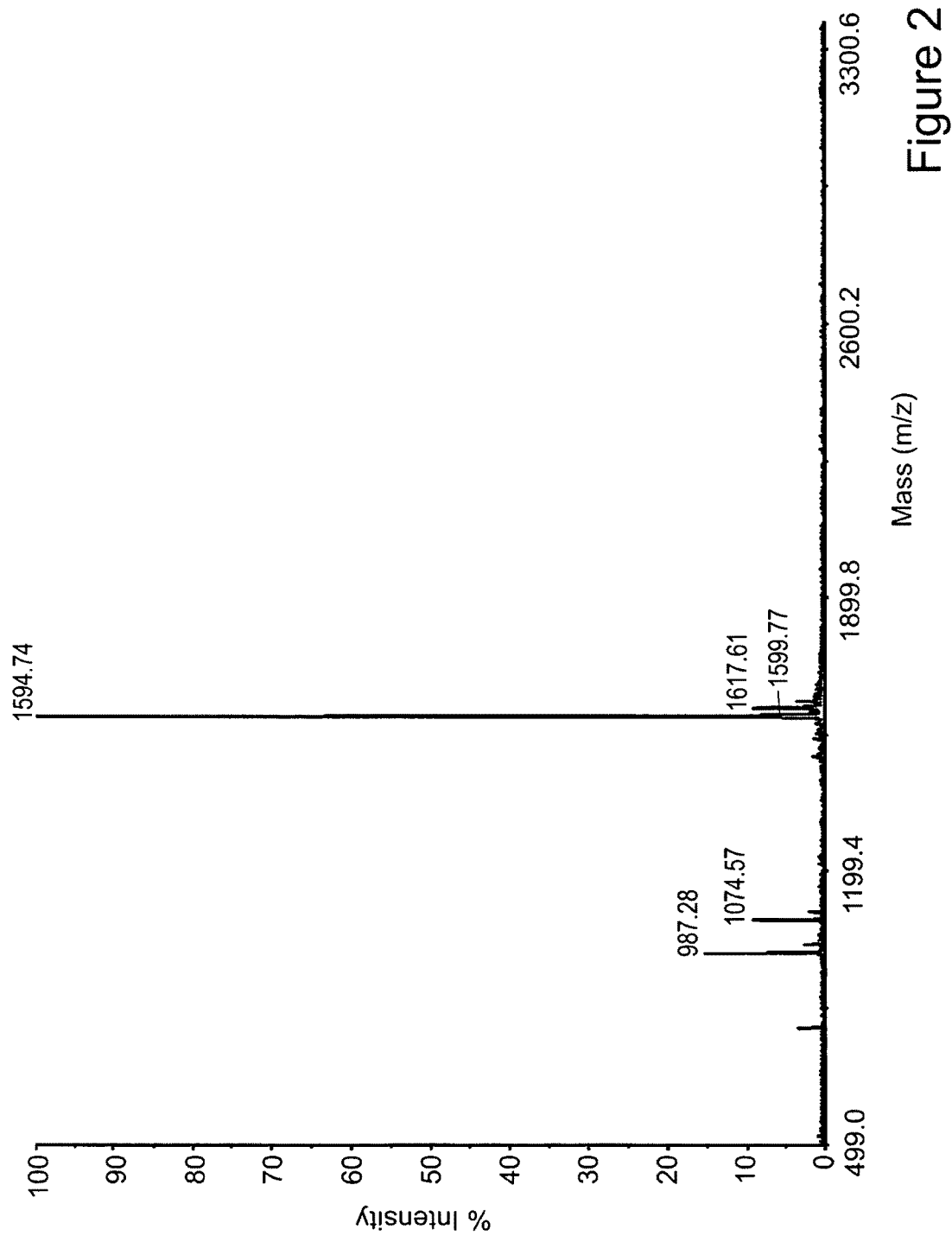
FIG. 2 shows a spectrum showing the correct mass of the $IGF_{28-41cys}$ peptide; 1594.74.

Reducing the stimulatory and anti-apoptotic action of IGF-1 via continuously present anti-IGF-1 antibodies is a rationally plausible preventive therapy for cancer in part because of the following rational. Dietary restriction, which can prolong lifespan and inhibit carcinogenesis, lowers IGF-1 levels in both humans and animals. Conversely, the protective action of dietary restriction on cancer progression in animals is nullified by IGF-1 supplementation (Dunn, S. E., et al., *Cancer Res* 57:4667-4672 (1997), Kari, F. W., et al., *J Nutr Health Aging* 3:92-101 (1999)).

The present invention is not limited to any particular theory of operation. However, the applicant presents the following merely for a better understanding of the present invention.

Several mutations that extend or shorten lifespan in diverse species, including nematodes, fruit flies, mice, and possibly humans, disturb endocrine signaling routes in the IGF-1 pathway (Kenyon, C., *Cell* 120:449-460 (2005); Holzenberger, M., et al., *Nature* 421:182-187 (2003); Vijg, J., and Y. Suh., *Annu Rev Med* 56:193-212 (2005); Butler, R. N., et al., *J Gerontol A Biol Sci Med Sci* 58:581-584 (2003); Dumble, M., et al., *Ann NY Acad Sci* 1019:171-177 (2004); Maier, B., et al., *Genes Dev* 18:306-319 (2004); Hursting, S. D., et al., *J Nutr* 134:2482S-2486S (2004)). Some mutations which perturb the IGF-1 signaling pathway significantly delay the onset of tumors in mice. Unfortunately the application of gene therapies to humans has not yet become commonplace. What is needed is a simple and safe vaccination procedure that will increase longevity and prevent cancer development and recurrence by selectively modulating IGF-1 levels in the body.

The longevity field provides research studies that indicate IGF-1 signaling may be important in lifespan extension. For example, one study showed that heterozygous IGF-1 receptor knockout mice, Igfr1$^{+/-}$, had a 33% (female) and 16% (male) increased lifespan compared to wild-type mice (Holzenberger, supra). This suggests that reducing IGF-1 signaling to half of normal levels may be sufficient to produce a measurable extension of lifespan in mice. Importantly, those mice did not develop dwarfism and were essentially normal in terms of activity, reproduction, metabolism, etc. However, homozygous null mutants, Igfr1$^{-/-}$, were not viable, indicating that some degree of IGF-1 signaling is essential, at the very least for proper embryogenesis.

Another study examined the combined longevity effects of mutation plus calorie restriction in mice (Bartke, A., et al., Nature 414:412 (2001)). This research used Ames dwarf mice that live ~60% longer than wild-type apparently because they have reduced plasma IGF-1 as well as other hormone levels. Calorie restriction usually lowers IGF-1 levels in mice by 35% and concomitantly increases longevity ~30%. Combining both factors in this experiment demonstrated that the already extended lifespan of Ames mice was prolonged further by a calorie-restricted diet. A simple interpretation of that result would propose that lifespan is increasingly lengthened as IGF-1 levels are progressively lowered. However, based on the shape of the survival curves (Bartke, A., et al., Nature 414:412 (2001)), the authors might argue that the two pathways to longevity are related but not necessarily identical.

Animals have been passively immunized with different isolated antibody preparations directed against IGF-1 and its receptor (Schurmann, A., et al., *Experientia* 52:55-59 (1996); Spencer, G. S., et al., Endocrinology 128:2103-2109 (1991); Koea, J. B., et al., J Endocrinol 135:279-284 (1992); Stewart, C. E., et al., Endocrinology 133:1462-1465 (1993); Kerr, D. E., et al., J Endocrinol 124:403-415 (1990); Cohen, B. D., et al., Clin Cancer Res 11:2063-2073 (2005); Araki, K., et al., Intl J Cancer 118:2602-2608 (2006); Goya, M., et al., Cancer Res 64:6252-6258 (2004); Miyamoto, S., et al., Clin Cancer Res 11:3494-3502 (2005)). However, none of these short-term, passive treatments were utilized in the context of a lifespan extension.

Therapeutic vaccines were first used in 1796 when Edward Jenner vaccinated people to protect them from contracting smallpox. Today there are numerous vaccines that are being used to safeguard us from a vast array of diseases. Table I provides a partial listing of those diseases and their therapeutic targets. The list serves to illustrate that most vaccines are directed against pathogenic invaders that present foreign antigens, which are new to the immune system.

TABLE I

Therapeutic Vaccines Currently in Use or Development

| Attenuated Virus or Viral Antigens |
| --- |
| Smallpox |
| Polio |
| Human Papillomavirus |
| Measles |
| Hepatitis A |
| Influenza |
| Rabies |
| Bird Flu |
| HIV (AIDS) |
| Bacterial Toxoids |
| Diphtheria |
| Tetanus |
| Bacteria or Bacterial Components |
| Tuberculosis |
| Hepatitis B |
| Pertussis |
| Pneumonia |
| *Helicobacter pylori* |

Recent advances in vaccine therapy include vaccines intended to elicit antibodies that bind to and neutralize naturally occurring molecules in the body, not foreign antigens. Examples of these novel "self-antigen" targets include β-amyloid (Raso, V., U.S. Pat. No. 6,582,945 (2003); Raso, V., U.S. Pat. No. 6,872,554 (2005)), an Alzheimer's disease associated peptide and ghrelin (WO/2007/092023), a hunger-inducing peptide hormone related to obesity.

The vaccination protocol described herein offers some very unique advantages as a cancer preventive intervention. There is a strong precedent for successfully using immunization as a therapeutic, especially for human diseases. The immune response has evolved expressly to remove or neutralize unwanted substances in the body and it does so with exquisite specificity. The immune system is designed to provide long-term protection for the body. This enduring nature of the immune response is an important attribute because a cancer preventive treatment likely needs to extend throughout much of a person's adult lifetime to prevent dormant or precancer cells from becoming active and/or undergoing transformation at any point in time. After a simple, inexpensive vaccination, the body can continuously produce therapeutic antibodies. Unlike most drugs, daily ingestion or injection is not required to maintain steady state concentrations within the body. Antibodies do not have to be replenished on a daily basis to maintain steady state concentrations. Since antibodies are naturally occurring proteins, the adverse side effects that often accompany any introduction of drugs or other foreign substances into the system are precluded. Thus a vaccine protocol is ideally suited to the task, given the fact that any cancer prevention treatment would most likely have to continue throughout most of the adult years.

Though IGF-1 is essential throughout embryogenesis and for spurts of statural growth during childhood, its necessity in adult life is much less compelling. IGF-1 has been linked to both carcinogenesis and length of lifespan. Lowering the levels of circulating IGF-1 will retard the progression and metastatic potential of a number of cancers. The present invention involves a simple, safe and inexpensive vaccination procedure for inducing specific anti-IGF-1 antibodies. The induced, endogenous antibodies circulate in the blood and serve as a continuously present therapeutic for suppressing the stimulatory activity of IGF-1 in the body. Antibody-sequestered IGF-1 is trapped in the blood stream until cleared and thereby rendered incapable of interaction with receptors on its target tissues and cancer cells.

The teachings herein show that the reducing the stimulatory and anti-apoptotic action of IGF-1 via continuously present anti-IGF-1 antibodies is, in one embodiment, an effective prevention therapy for cancer. Thus, described herein is a method for treating, delaying, reducing or preventing cancer in an adult human. The cancer patient or person at risk for cancer is vaccinated with an IGF-1 based antigen that stimulates the production of antibodies in the blood, the antibodies being specific to human IGF-1. The administered antigen can be the IGF-1 protein, a hydrolysis transition state analog of IGF-1, or an immunogenic portion of either. As is detailed in the Exemplification section, LPV-IGF$_{1-16}$, LPV-IGF$_{22-35}$, LPV-IGF$_{29-42}$, LPV-IGF$_{56-70}$, KLH-IGF$_{28-41}$, KLH-IGF$_{22-33}$, KLH-IGF$_{30-38}$, KLH-IGF$_{29-42}$, KLH-IGF$_{22-35}$, KLH-IGF$_{1-6}$, KLH-IGF$_{61-70}$, KLH-IGF$_{1-16}$, KLH-IGF$_{56-70}$, KLH-IGF$_{30-38}$, KLH-IGF$_{61-70}$, KLH-IGF$_{29-42}$, KLH-IGF$_{56-70}$, Qβ-IGF$_{28-41}$, Qβ-IGF$_{22-33}$, Qβ-IGF$_{30-38}$, Qβ-IGF$_{29-42}$, Qβ-IGF$_{22-35}$, Qβ-IGF$_{1-6}$, Qβ-IGF$_{61-70}$, Qβ-IGF$_{1-16}$, Qβ-IGF$_{56-70}$, Qβ-IGF$_{30-38}$, Qβ-IGF$_{61-70}$, Qβ-IGF$_{29-42}$ and Qβ-IGF$_{56-70}$ are specific examples of antigens of the present invention that can be used in the active immunization method in the prevention, reduction, delay of onset and treatment of cancer. Tables III and IV show that mice vaccinated with IGF-1 antigens of the vaccines of the present invention produced antibodies specific to the targeted IGF-1 epitopes even though the IGF-1 hormone is a self antigen.

Another embodiment of the method comprises administering a nucleic acid construct which encodes the antigen, rather than administering the antigen itself. The nucleic acid construct can be a DNA expression construct or an RNA construct.

Vaccinations preferably are be initiated in early adult life when IGF-1 is no longer needed for growth and vital functions, to persons at known risk for specific types of cancer or to persons diagnosed with cancer or persons who are in remission after conventional cancer treatment. The anti-IGF-1 immunotherapy of the present invention and its beneficial effect could be maintained indefinitely via periodic booster injections, if necessary. In the absence of satisfactory treatments for most cancers, prevention becomes a reasonable means to lower the incidence of this disease or reduce diagnosed tumors. In many cases this is preferable to finding new treatments because a modest delay or reduction in neoplastic development can lead to a substantial reduction in the frequency of clinically relevant disease. By continuously neutralizing the proliferation and survival benefits that IGF-1 provides to cancer cells, this IGF-1 vaccine approach provides long-term prevention of cancer initiation, progression and recurrence (for example, during remission following conventional cancer therapy). The immunotherapy compositions and methods of the present invention block IGF-1 receptor-mediated signaling in a safe and controllable manner. The immunotherapy compositions and methods of the present invention may also be administered sequentially or simultaneously with conventional therapies.

It is demonstrated herein that active immunization with an IGF-1 peptide vaccine produces circulating antibodies that can tightly bind IGF-1 in the serum. Thus, in an immunized animal, the sequestered IGF-1 is trapped in the blood stream until cleared and rendered unavailable to its target tissues. Additionally, the antibodies elicited by some of these vaccines of the present invention are directed against precise sites on the IGF-1 molecule that interact with its receptor. Therefore, by blocking IGF-1's ability to bind to the receptor, the antibodies prevent IGF-1 signaling and any mitogenic cellular responses that may result. Another class of antibodies of the present invention target the interaction between IGF-1 and its binding proteins. Included in the invention is the immune complex formed when a human anti-IGF-1 antibody binds to human IGF-1. The formation of this immune complex specifically interferes with the binding between IGF-1's receptor-binding epitopes and the IGF-1 receptor.

As is shown in the Exemplification section, below, one embodiment of the vaccine of the present invention is composed of an IGF-1 peptide coupled to a maleimide activated keyhole limpet hemocyanin (KLH) or Qβ viral capsid (Qβ) carrier. Applicants believe that these novel conjugate vaccines, the IGF-1-peptide-KLH conjugate and the IGF-1-peptide-Qβ conjugate, are not currently available. Additionally, another embodiment of the present invention is directed towards self-adjuvanting IGF-1 lipopeptide vaccines, as described below.

The IGF-1-specific antibodies elicited by active immunization with this vaccine constitute a continuously present therapeutic that suppresses this hormone's biological activity. Like dietary restriction and mutational modifications that reduce IGF-1 signaling, this immuno-neutralization approach will both extend lifespan and delay de novo carcinogenesis or any relapse following successful treatment and remission as well as slowing tumor growth rate. Antibodies are sustained in the circulation for long periods (years) following successful vaccination. The steadily maintained presence of anti-IGF-1 antibodies will ensure that this mitogenic hormone remains unavailable to cancer cells whenever they arise or require stimulation. Anti-IGF-1 antibody therapy and its beneficial effects can be maintained indefinitely via periodic booster injections. A simple periodic booster vaccination restores high antibody levels if or when they decline. The Exemplification describes a study in which, one month after a booster shot, the immune response was amplified approximately 5-10-fold in mice.

Periodic vaccinations, as well as initial vaccinations, may be administered by injection or other means known in the art (e.g., oral or nasal administration). The antigen may be delivered in an appropriate adjuvant formulation. Appropriate adjuvants are known by those skilled in the art. Blood samples may be taken at intervals and checked for antibody titer. This sustained anti-IGF-1 intervention is designed to delay or prevent spontaneous malignancies so monitoring the antibody titer in the patient can be important.

In addition to active immunization with IGF-1 antigens, patients can similarly be protected and treated for cancer via passive immunization with anti-IGF-1 antibodies. Another embodiment of the invention includes treating, delaying, reducing or preventing cancer by administering human or humanized antibodies which specifically bind human IGF-1. The antibodies may be monoclonal antibodies and/or single chain variable fragment (scFv) antibodies. A person having ordinary skill in the art will be familiar with recent advances in alternatives to antibodies, such as Spiegelmers and selective peptides. The claimed invention includes the use of these antibody alternatives which specifically bind human IGF-1 when administered to a human under conditions appropriate for direct contact with endogenous IGF-1. The administration of antibodies, Spiegelmers, and/or selective peptides can be repeated as often as necessary to maintain circulating levels in the blood such that IGF-1 mediated signaling is substantially reduced.

Spiegelmers are nucleic acids that are capable of binding specific target sites on molecules (similarly to antibodies). However, unlike traditional aptamers, Spiegelmers are designed to resist degradation by endogenous nucleases. This is because they are constructed from mirror image L-oligonucleotides (Klussmann, et al., Nat. Biotechnol. 14:112-1115, 1996; Vater and Klussmann, Corr. Opin. Drug Discov. Devel. 6:253-261, 2003).

Selective peptides are peptides designed to bind to specific target moieties (Chen, et al., Science 79:851-853, 1998 and references therein).

In addition to its cancer delaying, reducing or preventive application, the IGF-1 vaccine has potential for use in extending lifespan. Anti-IGF-1 antibodies can also be used as an active or passive form of immunotherapy to increase longevity. Anti-IGF-1 antibodies sequester or inactivate IGF-1 in the blood so that its ability to bind its receptor and signaling are suppressed. Antibodies that either tightly bind IGF-1 or catalytically cleave IGF-1 will destroy the activity of circulating IGF-1 and prevent receptor-mediated signaling in a controllable manner.

For longevity treatment, antibody therapy should begin in adult life when IGF-1 is no longer needed for growth. Longevity intervention would likely have to extend throughout much of an adult patient's lifetime. Accordingly, antibodies are sustained in the circulation for long periods (years) following successful vaccination. The steadily maintained presence of anti-IGF-1 antibodies will ensure that the action of this mitogenic hormone remains suppressed. This mimics the situation encountered when using long-term calorie restriction or permanent genetic modifications to reduce IGF-1 signaling in the body thereby preventing, reducing or delaying cancer or extending lifespan.

To extend lifespan in an adult warm-blooded animal, the invention includes methods whereby selected monoclonal or scFv antibodies, Spiegelmers, and/or selective peptides are administered to patients by passive immunization such that IGF-1 is inactivated or suppressed. To maintain circulating levels in the blood, these specific binding molecules can be administered intravenously by periodic bolus injection or by sustained infusion using a pump. The method includes antibodies, Spiegelmers, and selective peptides that bind IGF-1, a hydrolysis transition state analog of IGF-1 or an immunogenic portion of either peptide. The invention also includes methods whereby the binding of the anti-IGF-1 antibodies to IGF-1 interferes with the receptor binding epitopes of IGF-1 and also antibodies designed to interfere with interaction of IGF-1 with its protein.

In another embodiment, patients are actively immunized with IGF-1 based antigens or IGF-1 transition state analog based antigens so that the patients establish endogenous antibodies to IGF-1. The antigens used can include IGF-1, the hydrolysis transition state analog of IGF-1, or immunogenic portions of either peptide. As is detailed in the Exemplification Section, LPV-IGF$_{1-16}$, LPV-IGF$_{22-35}$, LPV-IGF$_{29-42}$, LPV-IGF$_{56-70}$, KLH-IGF$_{28-41}$, KLH-IGF$_{22-33}$, KLH-IGF$_{30-38}$, KLH-IGF$_{29-42}$, KLH-IGF$_{22-35}$, KLH-IGF$_{1-6}$, KLH-IGF$_{61-70}$, KLH-IGF$_{1-16}$, KLH-IGF$_{56-70}$, KLH-IGF$_{30-38}$, KLH-IGF$_{61-70}$, KLH-IGF$_{29-42}$, KLH-IGF$_{56-70}$, Qβ-IGF$_{28-41}$, Qβ-IGF$_{22-33}$, Qβ-IGF$_{30-38}$, Qβ-IGF$_{29-42}$, Qβ-IGF$_{22-35}$, Qβ-IGF$_{1-6}$, Qβ-IGF$_{61-70}$, Qβ-IGF$_{1-16}$, Qβ-IGF$_{56-70}$, Qβ-IGF$_{30-38}$, Qβ-IGF$_{61-70}$, Qβ-IGF$_{29-42}$ and Qβ-IGF$_{56-70}$ are specific examples of antigens that can be used in the active immunization method. These antibodies can be, in certain embodiments, conjugated to carrier proteins such as KLH or Qβ or incorporated into lipopeptide vaccines.

A person having ordinary skill in the art will be aware that multiple means of vaccine administration as well as DNA vaccines can be employed. Antibodies can be administered by periodic bolus or with a pump or by vaccine with the antigen or DNA and periodic boosters. Vaccines may also be administered orally or nasally. DNA vaccines can induce the body to produce IGF-1 specific antibodies thus forming a longevity therapeutic that is present on a continuous basis. Patients treated with antibodies or treated to produce antibodies will have reduced and/or controlled levels of active IGF-1 in their blood and, as a result, endocrine signaling will be disrupted producing a corresponding increase in the patients' lifespan and/or reduction in tumor generation or growth. During active immunization, a simple periodic booster vaccination would restore high anti-IGF-1 antibody levels if they decline. Since the induced antibodies are naturally occurring proteins, the adverse side effects associated with many drug regimens should be largely precluded. This lifespan increasing therapy can also be applied to other warm blooded animals including pets, farm, working and other animals and such uses of the invention are included in the methods. Additionally, kits complete with instructions are included in the present invention.

The present invention also contemplates the correlation of immunizing a warm blooded animal with a reduction in the growth of tumors, the prevention of the growth of tumors and the reduction in symptoms associated with aging. Such correlations can be made between treated subject(s) and control subjects and/or between treated subject(s) and historic data or between treated subjects before and after treatment. For example, when correlating with historic data, a treated subject may show a reduction in tumor growth, prevention of tumors or a reduction in one or more symptoms associated with aging as compared to comparable subjects on which data have been collected in the past or known from practitioner's experience. Symptoms associated with aging may include, but are not limited to, one or more of decreased life span, abdominal fat/truncal obesity, muscle wasting, thin skin and skin wrinkles, poor sleep, cognitive changes, mood changes, decreasing energy or stamina, lessened sexual performance, weak bones, reduced cardiac output, impaired kidney function and others known to those practiced in the art.

Biomarkers of aging are divided in three major categories. There are the ones which determine the biological age, e.g., skin elasticity and visual accommodation. There are markers which predict the remaining life expectancy; they include DHEA-S, hand grip strength, etc. Finally, there are factors which determine disease susceptibility, such as systolic blood pressure and glucose-tolerance tests. All of the biomarker tests can be classified either as laboratory tests (e.g., blood and urine tests) or as physical tests undertaken in a clinic. In the context of the present invention, they may all be used as indicators.

It is generally believed that seven major health areas are affected by aging: cardiovascular health, glucose regulation, brain function, muscle and skeletal health, endocrine function, immune system and oxidative stress. Biomarkers of aging are physical properties in the human body which indicate that the body is aging. It is indicators of the normal phenomena of growing old. They are not, however, simply things which change with age. In order to be called a biomarker, a factor has to satisfy a number of criteria. The best markers for aging are not susceptible to influence from the outside environment. For example, in the US cholesterol levels increase with age, but this is due to the nature of the American diet and is not characteristic for other parts of the world. Thus, a true biomarker would satisfy the following criteria. The marker must predict the rate of aging and be a better predictor of life span than chronological age. It should work both for humans and other species, such as laboratory animals. There is support from human clinical assessment and complementary research studies. The studies are based on a significant representative sample. The result is an association with aging. A relatively narrow standard deviation is present. So far, around 24 factors have met the criteria and can be considered biomarkers (see, below). They may be indicated especially for males or for females and figures may vary between the sexes. One skilled in the art will understand the methods and ranges applicable to an indication of aging.

1. 17-ketosteroid/17-hydroxycortiosteroid ratio (male)
2. Ascorbic acid level
3. Basal Metabolic Rate
4. Blood pressure—pulse
5. Blood pressure—systolic
6. Body Mass Index (female)
7. Caries index
8. Creatinine clearance
9. DHEA-S
10. Fibrinogen level
11. Hair baldness (male)
12. Hair grayness
13. Handgrip strength
14. Hemoglobin A1C
15. Lung capacity—FEV1 (forced expiratory volume in one second)
16. Lung capacity—FVC (forced vital capacity)
17. Maximum oxygen update (male)
18. Near vision acuity
19. Noradrenaline—plasma level (male)
20. Peridontal index
21. PSA (prostate specific antigen) total (male)
22. Skin elasticity
23. Free testosterone level (male)
24. Zinc—serum level In addition, there are also a number of secondary factors which may be considered biomarkers of aging. These include body flexibility, blood urea nitrogen, LDL cholesterol, melatonin levels, static balance, serotonin levels and others known to those skilled in the art. They are to a certain degree indicative of a person's biological age, but should not be confused with other general health factors, which do not have a clear association with age. Biomarkers of aging are divided in three major categories. There are the ones which determine the biological age, e.g., skin elasticity and visual accommodation. There are markers which predict the remaining life expectancy; they include DHEA-S, hand grip strength, etc. Finally, there are factors which determine disease susceptibility, such as systolic blood pressure and glucose-tolerance tests. All of the biomarker tests can be classified either as laboratory tests (e.g., blood and urine tests) or as physical tests undertaken in a clinic. In the context of the present invention, they may all be used as indicators.

Other factors are also known in the art as is evident by recent publications such as, for example, "Effect of 6-Month Calorie Restriction on Biomarkers of Longevity, Metabolic Adaptation, and Oxidative Stress in Overweight Individuals. A Randomized Controlled Trial" (Heilbronn, L. K., et al., *JAMA*. 2006;295:1539-1548).

Exemplification

Full-length human IGF-1, IGF-1 derived peptides, or hydrolysis transition state analogs of those peptides can be used to produce antigens for monoclonal antibody production in normal or humanized mice. These peptides can also be used to screen for single chain variable fragment (scFv) antibodies from human recombinatorial libraries. An scFv antibody retains the specificity of the original immunoglobulin but has its heavy and light chain variable regions fused together such that the antigen binding domain is a single peptide. Screened antibodies are characterized by binding and proteolytic assays. Those antibodies showing catalytic activity or high affinity for either the native or transition state analog IGF-1 peptide are selected.

Analysis of the structural and functional relationships of the IGF-1 protein (Denley, A., et al., Cytokine Growth Factor Rev., 16:421-439 (2005)) has facilitated the choice of appropriate target epitopes for inducing therapeutic anti-IGF-1 antibodies in both mice and humans. Only four positions in the IGF-1 sequence differ in these two species (FIG. 1). Several mouse and human IGF-1 vaccine peptides were selected based upon different criteria (FIG. 1). Epitopes $IGF_{28-41}$, $IGF_{22-33}$, and $IGF_{30-38}$, $IGF_{29-42}$ and $IGF_{22-35}$, were chosen so that the antibodies induced by them would specifically block IGF-1 binding to its cellular receptor. Epitopes $IGF_{1-6}$, $IGF_{61-70}$, $IGF_{1-16}$ and $IGF_{56-70}$ were chosen to elicit antibodies that inhibit the attachment of the IGF-1 binding proteins. The recognition site for binding the IGF-1 receptor is distinct from the recognition sites for binding the IGF-1 binding proteins. Additionally epitopes $IGF_{30-38}$, $IGF_{61-70}$, $IGF_{29-42}$ and $IGF_{56-70}$ were decided upon to exclude the possibility of inducing antibodies having cross-reactivity with insulin.

IGF-1 peptides are not intrinsically immunogenic but will elicit antibodies if they are chemically coupled to antigenic carrier molecules. KLH and Qβ virus-like capsid particles function effectively as carriers and have a history of use in clinical vaccine trials. KLH is a laboratory standard for that purpose. Qβ virus-like particles possess interesting properties and a potential for eliciting high-potency antisera. The 180, highly repetitive and organized capsid subunits allow for the display of multiple IGF-1 peptide epitopes on the surface of these particles. These viral carriers greatly improve B cell responsiveness, especially for self-antigens (Bachmann, M. F., et al. Science 262:1448-1451 (1993); Chackerian, B., et al., J Immunol 169:6120-6126 (2002)). Because of the apparent advantages of this virus-based carrier, we modified a previously described procedure (Cielens, I., et al., FEBS Lett 482:261-264 (2000); Koziovska, T. M., et al., Gene 137:133-137 (1993); Kozlovska, T. M., et al., Intervirology 39:9-15 (1996)) to produce the genetically engineered Qβ capsid particles IGF-1 vaccines of the present invention.

Figure 3:
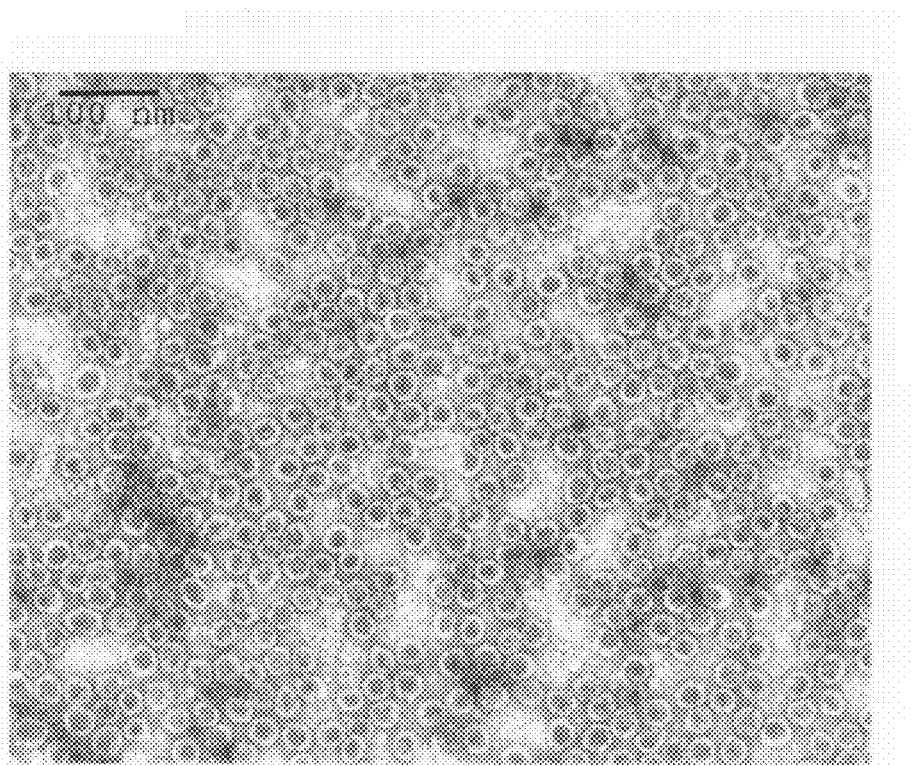
FIG. 3 shows an electron micrograph of exemplifications of the Qβ capsids of the present invention (top) and a structural model of the Qβ capsid (bottom).
Figure 3:
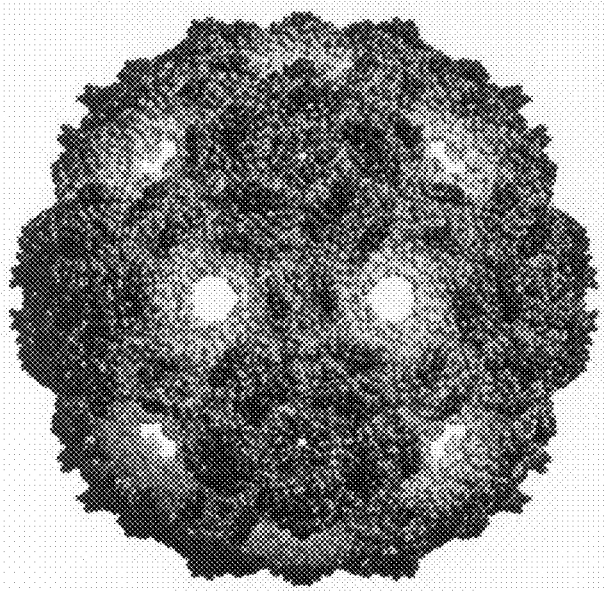
Figure 4:
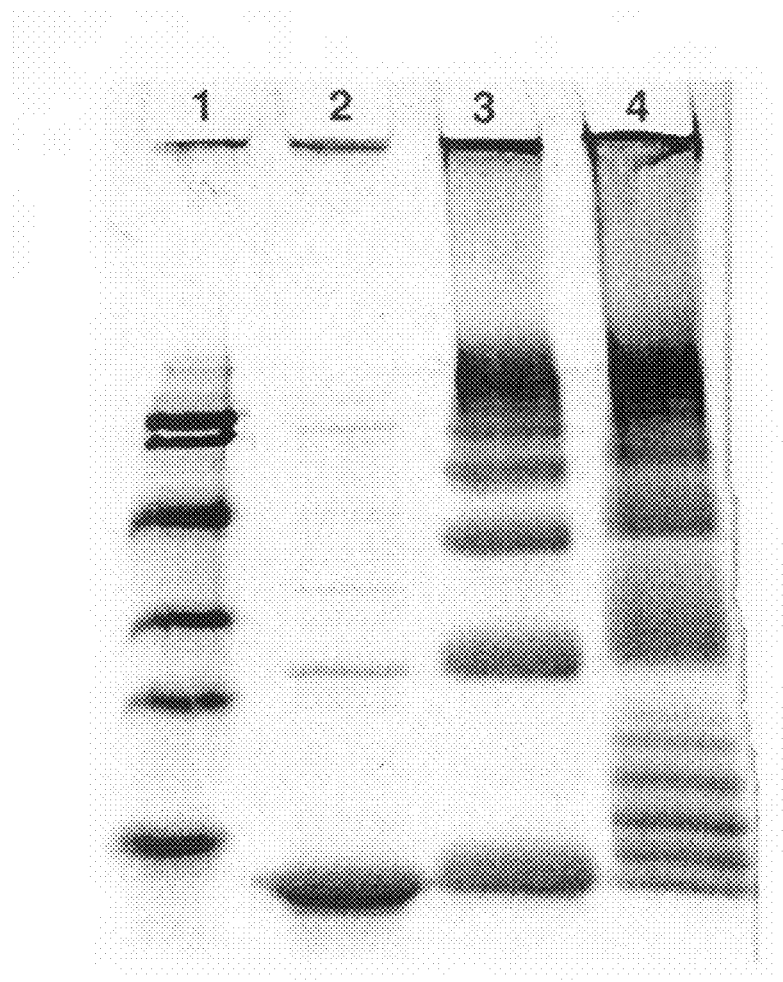
FIG. 4 shows an SDS-PAGE of Qβ-$IGF_{22-33cys}$ conjugate. Lanes: 1, Stds; 2, Qβ; 3, mal-Qβ; 4, Qβ-$IGF_{22-33cys}$. Arrows indicate 14 kDa subunit with IGF-1 peptides. The multiple shift in the position of this lowest band in Lane 4 indicates that the coat protein constituting the virus was variably substituted with 0, 1, 2, 3 and 4 IGF-1 peptides/subunit.

A novel self-adjuvanting vaccine strategy (Chua, B. Y., W. Zeng, Y. F. Lau, and D. C. Jackson. 2007. *Vaccine* 25:92-101)

has the potential to simplify the vaccination procedure and circumvent many of the side effects associated with immunization (e.g., inflammation). This totally synthetic approach incorporates the IGF-1 epitope, a helper T cell epitope and a tripalmitoyl-S-glyceryl cysteine (Pam3Cys) moiety into a single branched lipopeptide (FIG. 6). This new approach facilitates both switching between different IGF-1 epitopes and constructing scrambled-sequences for control vaccines. An alternative Pam2Cys moiety with the chemical name S-[2, 3-bis(palmitoyloxy)propyl]cysteine (Chua, B. Y., W. Zeng, Y. F. Lau, and D. C. Jackson. 2007. *Vaccine* 25:92-101) is also effective in the context of the present invention. These vaccines obviate the need for irritating adjuvant formulations, allow subcutaneous injection and thereby greatly improve the vaccine's translatability to human therapy.

These different epitope vaccines suppress IGF-1 activity in mice to greater or lesser extents dependent upon the antibodies and titers induced. This gave us an opportunity to test whether or not the extent of lifespan extension or cancer prevention, reduction or delay is inversely proportional to bioavailable IGF-1 levels in vaccinated mice.

Production of IGF-1 Vaccines

Synthesize IGF-1 Epitope Peptides

After examining the structure/function relationships of the IGF-1 protein (Denley, A., et al., Cytokine Growth Factor Rev 16:421-439 (2005)) several peptides were chosen that define key sites on the molecule (FIG. 1). The carefully selected IGF-1 peptides were synthesized at our Boston Biomedical Research Institute (BBRI) facility, purified using HPLC and analyzed by mass spectroscopy (for example, see FIG. 2). Several peptides had a cysteine residue (C) within their sequence ($IGF_{1-6}$, $IGF_{7-18}$, $IGF_{38-47}$, $IGF_{48-60}$, and $IGF_{61-70}$) while an extra cysteine was added to the peptides that did not already have one ($IGF_{22-33cys}$, $IGF_{28-41cys}$, and $IGF_{30-38cys}$). The peptides were then covalently coupled via their free sulfhydryl group to maleimide activated keyhole limpet hemocyanin (KLH) or maleimide activated Qβ virus-like particles (Qβ) (Spohn, G., et al., J Immunol 175:6211-6218 (2005)). This created IGF-1 peptide antigens needed for the immunization of test animals. Most of these IGF-1 peptides are identical in both humans and mice. However, both forms were synthesized where they diverged. Mice that have been actively immunized with this IGF-1-based antigen can be expected to produce endogenous antibodies at concentrations between ~1-10×$10^{-6}$ M in the serum (Hu, J G, et al. *Chem Pharm Bull* (Tokyo) 37: 3042-3046 (1989)). The level of IGF-1 in normal mice is typically ~3×$10^{-8}$ M (Yakar, S., et al., *Proc Natl Acad Sci USA* 96:7324-7329 (1999)) and consequently any pools of free or releasable hormone would be completely antibody-bound in a well-immunized mouse having a large excess of antibody. Thus the blood levels of available, active IGF-1 will be greatly reduced in anti-IGF-1 antibody-producing mice.

Production of IGF-1 Lipopeptide Vaccines

After examining the structure/function relationships of the IGF-1(Denley, A., et al., 2005. *Cytokine Growth Factor Rev* 16:421-439) protein we chose several peptides that define key sites on the molecule for the production of lipopeptide vaccines (FIG. 1). $IGF_{29-42}$, and $IGF_{22-35}$ were selected because they should elicit antibodies directed against sites on IGF-1 which specifically interact with its cellular receptor. Thus, these would potentially induce blocking antibodies that prevent IGF-1 signaling. Others like $IGF_{1-16}$ or $IGF_{56-70}$ are meant to elicit antibodies that will inhibit attachment of the IGF-1 binding proteins, which are needed to effectively transport IGF-1 out of the blood stream. Peptides such as $IGF_{29-42}$ and $IGF_{56-70}$ also exclude the possibility of inducing antibodies having cross-reactivity with insulin.

Initially the carefully selected IGF-1 peptides were covalently coupled via their free sulfhydryl group to maleimide activated keyhole limpet hemocyanin (KLH) and maleimide activated Qβ virus-like particles (Qβ) (Kozlovska, T. M., et al., 1996. *Intervirology* 39:9-15.). That procedure was necessary because small IGF-1 peptides are not inherently immunogenic and must be coupled to antigenic carrier molecules. Although much of our early preliminary data has been generated using those conventional vaccines, we have now opted to switch over to a much more sophisticated lipopeptide vaccine methodology.

We adopted this elegant self-adjuvanting vaccine strategy (Chua, B. Y., W. Zeng, Y. F. Lau, and D. C. Jackson. 2007. *Vaccine* 25:92-101) to simplify the vaccination process and to greatly reduce its potential generalized side effects. These new lipopeptide vaccines (LPV) incorporated an IGF-1 epitope, a helper T cell epitope and a tripalmitoyl-S-glyceryl cysteine (Pam3Cys) moiety into a single branched lipopeptide (FIG. 6).

Those composite vaccines eliminate the need for a KLH or Qβ carrier and the ensuing anti-carrier antibodies they would elicit. They also allow for subcutaneous (s.c.) administration in saline without using any potentially toxic or irritating adjuvant formulations (e.g., complete Freund's adjuvant; CFA). These features greatly improve the translatability of the vaccines to human therapy. Importantly, antibody titers induced by lipopeptide vaccines are as high as achieved with CFA (Chua, B. Y., W. Zeng, Y. F. Lau, and D. C. Jackson. 2007. *Vaccine* 25:92-101), which is considered the gold standard in terms of eliciting a strong immune response. These vaccines are reported to activate immune cells in a Toll-like receptor-2-dependent manner (Chua, B. Y., W. Zeng, Y. F. Lau, and D. C. Jackson. 2007. Vaccine 25:92-101).

Characterization of the Lipopeptide Vaccines:

The IGF-1 lipopeptides, LPV-$IGF_{1-16}$, LPV-$IGF_{22-35}$, LPV-$IGF_{29-42}$ and LPV-$IGF_{56-70}$ (Chua, B. Y., W. Zeng, Y. F. Lau, and D. C. Jackson. 2007. *Vaccine* 25:92-101) were synthesized at our BBRI facility, purified using HPLC and analyzed by mass spectroscopy. They have been characterized as lipopeptides by staining with Oil Red O after PAGE on 18% gels. Alternative IGF-1 epitopes and different T cell epitopes can be incorporated into this scheme, as well as, scrambled-sequence epitopes for control vaccines. This panel of lipopeptides will allow us to determine which target epitope is optimal to reduce IGF-1 activity, prevent, reduce or delay cancer and prolong lifespan.

Assemble Viral Capsid Carrier Particles

A previously described procedure was modified (Cielens, I., et al. FEBS Lett 482:261-264 (2000); Kozlovska, T. M., et al. Gene 137:133-137 (1993); Kozlovska, T. M., et al. Intervirology 39:9-15 (1996)) to produce genetically engineered Qβ virus-like capsid particles. These particles are ideal to use as a highly immunogenic carrier for the IGF-1 peptide vaccines. Briefly, appropriate DNA primers was synthesized for use in RT-PCR to selectively remove the coat protein gene from Qβ RNA bacteriophage (obtained from the American Type Culture Collection repository). The coat protein gene was ligated into the appropriate restriction sites of a vector that was then used to transform the B121 *E. coli* secretion strain. DNA sequencing established that the gene was correctly transferred and in frame to give the proper amino acid sequence of the monomer coat protein subunit.

Cultures of these induced bacteria produced copious amounts of properly assembled virus capsid particles (FIG. 3, top) that were released upon lysis using freeze thawing with lysozyme. Purification was achieved by precipitation using 50% ammonium sulfate and then separation on a Superose 6 sizing column. The isolated virus-like particles were characterized by SDS-PAGE under reducing conditions and an appropriate sized 14 kDa virus subunit protein was found (FIG. 4, Lane 2). Proper Qβ capsid assembly was verified at our BBRI protein structure facility after negative staining with uranyl acetate and examination using electron microscopy (FIG. 3, top). Those combined analytical results indicated that 180 of the 14 kDa subunits assembled into an icosahedral protein shell (Golmohammadi, R., et al., Structure 4:543-554 (1996)) as depicted by X-ray crystallography (FIG. 3, bottom).

Attach IGF-1 Peptides to Antigenic Carriers

Since the small IGF-1 peptides are not inherently immunogenic they had to be coupled to antigenic carrier molecules. We chose to use both KLH and Qβ virus-like capsid particles for this purpose because of their proven effectiveness and since they have been previously tested as carriers in clinical trials. Several of the IGF-1 cysteine peptides were thioether-linked to either commercially available maleimido-KLH or to maleimido-derivatized Qβ virus-like capsid particles (Spohn, G., et al., J Immunol 175:6211-6218 (2005)). Standard reaction conditions supplied by the manufacturer or previously described (Spohn, G., et al., J Immunol 175:6211-6218 (2005)) were used to derivatize the carriers and couple the peptides. Maleimido-carriers reacted with cysteine rather than IGF-1 peptides were produced to serve as control antigens.

Purify and Characterize the IGF-1 Conjugate Vaccines

The IGF-1 peptide-KLH conjugates were purified by extensive dialysis to remove any un-reacted peptide plus other reaction components. We attached $IGF_{22\text{-}33cys}$ to Qβ and isolated this conjugate by centrifugation, which forms pellets of the modified viral particles, thus isolating IGF-1 substituted Qβ from any unreacted free peptide. SDS-PAGE analysis under reducing conditions (FIG. 4) verified that the IGF-1 peptide (1.44 kDa) was covalently attached to the Qβ viral coat protein (14 kDa). The multiple shift in the position of this lowest band in Lane 4 indicated that the coat protein constituting the virus was variably substituted with 0, 1, 2, 3 and 4 IGF-1 peptides/subunit. Therefore each complete Qβ particle, which is composed of 180 of these coat subunits, had >180 IGF-1 peptides exposed on its surface. Neither unmodified Qβ capsids (Lane 2) nor chemically modified maleimido-Qβ (Lane 3) showed the multiple banding pattern (arrows) seen for the complete Qβ-$IGF_{22\text{-}33cys}$ conjugate (Lane 4).

Immunization of Mice with IGF-1 Vaccines

Vaccinate Mice with IGF-1 Conjugated KLH

Different groups of BALB/c mice were immunized with several of the IGF-1 peptides from our panel of epitope candidates individually conjugated to KLH. The immunization protocol was standard, using complete Freund's adjuvant for the primary injection and incomplete Freund's adjuvant for subsequent booster injections.

To make the emulsion for the initial immunization, 1 volume of Complete Freund's Adjuvant (vortexed to suspend the solids) plus 1 volume of the IGF-1-peptide-KLH conjugate in phosphate buffered saline was used. Subsequent Intraperitoneal booster immunizations at 1, 6, 12, 18, 24 and 30 months thereafter used 1 volume of Incomplete Freund's Adjuvant plus 1 volume of the IGF-1-peptide-KLH conjugate (20 μg) in phosphate buffered saline to make the emulsion. In the laboratory the water/oil mixture is passed rapidly through a double-hub needle until an emulsion is achieved. A Virtis high-speed homogenizer can be used to make a large volume of emulsion. Allowance should be made for significant loses due to the emulsion sticking to surfaces.

Initially three different IGF-1 conjugate vaccines were used for an assessment of immunogenicity. However, other supplementary KLH-IGF-1 conjugates can be used. In addition to the BALB/c strain we also vaccinated female C57BL/6J Tg(WapTAg) 1Knw mice which have been genetically modified to spontaneously develop soft tissue tumors when they are 6-13 months old. Experiments using this strain permit evaluation of whether our IGF-1 vaccine delays the development of carcinogenesis.

Lifespan extension trials use the recommended four-way cross CB6F1×C3D2F1 mice (Miller, R. A., and N. L. Nadon, et al., J Gerontol A Biol Sci Med Sci 55:B117-123 (2000); Nadon, N. L. et al., J Gerontol A Biol Sci Med Sci 61:813-815 (2006); Nadon, N. L., et al., Aging cell 5:9-15 (2006); Warner, H. R., et al., Mech Ageing Dev 115:199-207 (2000)) for vaccination with a chosen KLH-IGF-1 immunogen. One skilled in the art will understand that other mouse genotypes can be used. For example, if those stains of mice are not available then CB6F1 heterozygous mice can be used for the longevity testing of the chosen KLH-IGF-1 vaccine.

Vaccinate with IGF-1 Conjugated Viral Capsids

The characterization of the immune response elicited by the KLH-$IGF_{22\text{-}33cys}$ conjugate vaccine indicated that this peptide was an excellent exemplary candidate with which to proceed. Therefore we also coupled the $IGF_{22\text{-}33cys}$ peptide to maleimido-derivatized Qβ and immunized a group of BALB/c mice with the resulting Qβ-$IGF_{22\text{-}33cys}$ vaccine. Control mice were vaccinated with Qβ-cys. A standard immunization protocol was followed that used complete Freund's adjuvant for the primary injection and incomplete Freund's adjuvant for subsequent booster injections. All of the Qβ-IGF-1 conjugates in the panel of epitope candidates will be evaluated for the expected immune response.

Female C57BL/6J Tg(WapTAg) 1Knw mice may also be vaccinated with the Qβ-$IGF_{22\text{-}33cys}$ antigen and used to judge whether the IGF-1 vaccine delays the development of carcinogenesis.

Lifespan extension trials use the recommended four-way cross CB6F1×C3D2F1 mice for vaccination with the selected Qβ-IGF-1 immunogen. However, if those mice are not available then one skilled in the art will understand that mice of other genotypes may be used such as, but not limited to, CB6F1 heterozygous mice for the longevity testing of the chosen Qβ-IGF-1 vaccine.

Vaccinate Mice with Control Carriers

In the early experiments, non-immunized mice served as controls for the IGF-1 vaccinated mice. More recently we have begun to use cys-conjugated KLH and cys-conjugated Qβ to vaccinate separate sets of control mice. The maleimide groups on those control carriers were reacted with cysteine rather than with an IGF-1 peptide. These immunizations with cys-conjugated carriers have provided antisera with antibodies directed against the different carriers but not against the IGF-1 peptides. The use of such control animal groups and their sera helps to distinguish phenomena which are specifically due to the anti-IGF-1 immune response.

Monitor the Health of the Mice

Animals that have been immunized with the IGF-1 vaccines of the present invention could potentially develop health problems. IGF-1 is a self-antigen, thus autoimmune symptoms might develop. This possibility has not presented itself as a real problem for either mice or monkeys following long-term immunization with similar self-antigen peptide vaccines. No acute autoimmune effects were observed in the mice that were immunized and boosted with the IGF-1 vaccine.

IGF-1 signaling may be reduced in the body of the vaccinated mice and that could cause growth problems in younger animals. In addition insulin regulation of blood glucose levels might be disrupted if the induced anti-IGF-1 antibodies cross-react significantly with that important hormone.

Therefore the mice were monitored on a daily basis to see if they appear distressed or moribund. Signs may include decreased activity, hunched appearance, ruffled fur, respiratory distress, dehydration, and loss of weight and body condition. More specific laboratory assays that were used are designed to monitor and compare the control versus vaccinated groups vis-à-vis their growth (weight increase), glucose levels, etc. No overt health problems have been observed in any of the immunized mice even though many of them have been producing anti-IGF-1 antibodies for >7 months.

Figure 5:
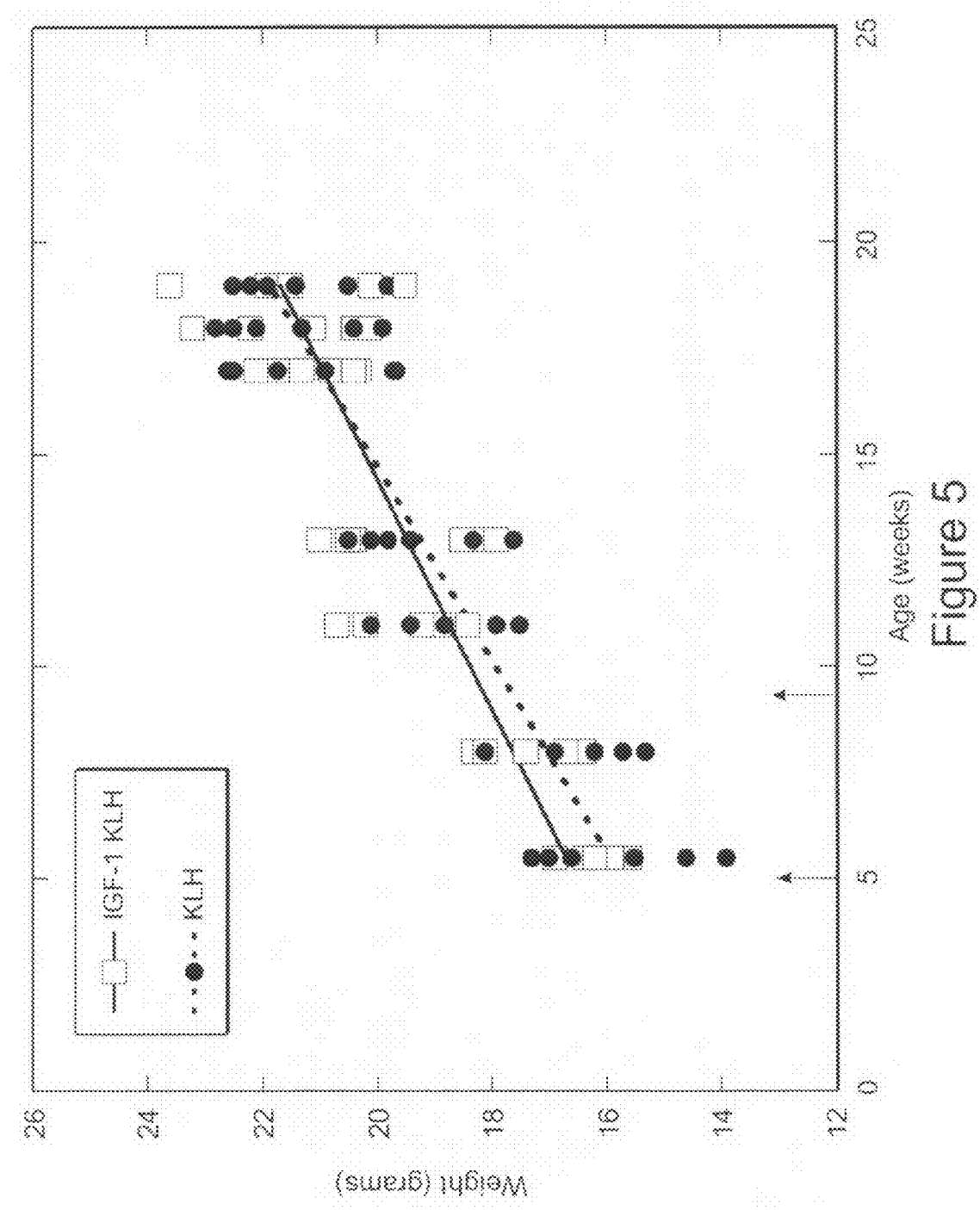
FIG. 5 shows growth of KLH-$IGF_{22-33cys}$ immunized mice (6) versus KLH immunized mice (6); arrows denote vaccination.

A growth comparison for control and KLH-IGF$_{22-33cys}$ immunized C57BL/6J Tg(WapTAg) 1Knw spontaneous tumor mice is shown in FIG. 5. This experiment was designed to determine if our IGF-1 vaccine delays the onset of carcinogenesis in that model system. There were no apparent growth changes between the control KLH and KLH-IGF-1 groups; both vaccinated at weeks 5 and 9 (arrows). Thus, immunization against IGF-1 did not stunt or otherwise negatively affect the growth of these mice.

There was a possibility for cross-reaction of anti-IGF-1 antibodies with insulin in vaccinated mice, which could produce diabetes. Therefore blood samples were taken and glucose analyses performed to determine if BALB/c mice producing anti-IGF$_{22-33cys}$ antibodies were compromised in terms of their insulin-controlled sugar levels. These mice had already received a primary injection and booster shot of the KLH-IGF$_{22-33cys}$ vaccine and they had been producing anti-IGF-1 antibodies for ~4 months. Table II shows the test results for each individual mouse. The average blood glucose value was 138±29 mg/dl and 142±41 mg/dl for the non-vaccinated mice and IGF-1-vaccinated mice, respectively. Thus, there was no significant difference between the non-immunized control and the IGF-1 immunized groups. Normal blood glucose levels in fed mice are about 144 mg/dl while concentrations ranging between 270-540 mg/dl are considered diabetic. If deemed necessary, one skilled in the art understands that glucose tolerance tests can also be performed on the mice to further evaluate any possible interference with insulin-mediated carbohydrate regulation.

TABLE II

Blood Glucose Levels in IGF-1 Vaccinated Mice[a]

| Mouse Injected with: | Glucose Level (mg/dl) |
|---|---|
| 1-No Vaccine | 105 |
| 2-No Vaccine | 131 |
| 3-No Vaccine | 143 |
| 4-No Vaccine | 174 |
| 5-IGF-1 Vaccine | 100 |
| 6-IGF-1 Vaccine | 134 |
| 7-IGF-1 Vaccine | 198 |
| 8-IGF-1 Vaccine | 136 |

[a]Glucose concentration was measured in whole blood (1 µl) using an electrochemical biosensor assay.

Immunize Mice with IGF-1 Lipopeptide Vaccines
Immunize with Self-adjuvanting IGF-1 Vaccines For conventional immunizations BALB/c mice were immunized with IGF$_{22-35cys}$ conjugated to maleimide-activated KLH (KLH-IGF$_{22-33cys}$). We used an intraperitoneal (i.p.) primary injection with 20 µg of the antigen emulsified in complete Freund's adjuvant followed one month later by an i.p. booster injection of the same antigen emulsified with incomplete Freund's adjuvant. The oil-water emulsion is hard to form and its high viscosity makes it difficult to inject into the peritoneal cavity. This can lead to death for some animals.

Immunization with the IGF-1 lipopeptide vaccines (LPV) is a much more compatible procedure since the lipopeptide is simply dissolved in saline and used as such. Thus, the LPV-IGF$_{22-35}$ (50 µg) was injected subcutaneously (s.c.) into BALB/c mice using saline as a vehicle in the absence of any adjuvant. That same process is repeated at intervals, as necessary, to boost the animal's immune response.

A lipopeptide formulation offers quite an advantage in terms of both its preparation and use, especially when vaccinating large numbers of animals, as would be the case for our longevity studies.

Vaccinate with Scrambled Control Lipopeptides

In our early experiments we made use of non-immunized mice or KLH and Qβ conjugated with cysteine or mercaptoethanol to serve as controls for the IGF-1-conjugate vaccinated mice. Control vaccines for the lipopeptide-based vaccines use scrambled IGF-1 sequences for incorporation into the lipopeptide construct (FIG. 6). The use of control animal groups and their sera helps to distinguish phenomena which are specifically due to the anti-IGF-1 immune response.

Monitor the Health of the Mice

The mice immunized with the lipopeptide vaccines were also monitored for outward signs of auto-immune disease and adverse growth effects, as above, with comparable results.

Characterization of the Antisera Elicited by the Various IGF-1 Vaccines

Compare Anti-IGF-1 Titers and Specificity

An ELISA protocol was used to evaluate the titer and IGF-1 epitope specificity of the various sera generated by the KLH-IGF-1 vaccines. The pure IGF-1 peptides or recombinant IGF-1 were adsorbed directly onto polyvinyl chloride microtiter well assay plates so that anti-IGF-1 antibodies were exclusively measured. Anti-carrier antibodies are not detected with these assays.

ELISA data presented in Table III indicates that four mice vaccinated with the KLH-IGF$_{22-33cys}$ antigen gave an appropriate immune response to the IGF$_{22-33cys}$ peptide when tested one month after their primary injection. This assay was designed to measure only the major IgG antibody response, not the other immunoglobulin classes. Immunized mice clearly produced antibodies that recognized the IGF-1 peptide with which they were vaccinated. Tests using IGF-1 epitope peptides other than IGF$_{22-33cys}$ showed no reaction with these antisera. Thus the vaccinated mice produced specific antibodies directed against the selected IGF-1 target epitope even though that hormone peptide is a self-antigen.

It was imperative to also demonstrate that these IGF$_{22-33cys}$ peptide-specific antibodies are able to bind to the whole, native IGF-1 molecule. Table III shows ELISA data obtained by using the mouse recombinant IGF-1 complete protein adsorbed onto the plate instead of the IGF$_{22-33cys}$ epitope peptide. Serum taken 1 month after the primary vaccination was diluted 1/100 for this assay. Subsequent analysis of sera drawn 1 month following the secondary booster injection showed detectable antibody levels following a 1/500 dilution. Thus the boost succeeded in amplifying the immune response approximately 5-10-fold in most of the mice.

TABLE III

Serum Antibodies Present in KLH-IGF$_{22-33cys}$ Vaccinated Mice[a]

| Mouse Injected with: | ELISA READING (O.D. 450 nm) | |
|---|---|---|
| | IGF-1$_{22-33cys}$ Peptide | Recombinant IGF-1 |
| 1-No Vaccine | 0.093 | 0.293 |
| 2-No Vaccine | 0.147 | 0.416 |
| 3-KLH-IGF$_{22-33cys}$ + CFA | 2.694 | 2.036 |
| 4-KLH-IGF$_{22-33cys}$ + CFA | 2.584 | 1.561 |
| 5-KLH-IGF$_{22-33cys}$ + CFA | 2.674 | 1.084 |
| 6-KLH-IGF$_{22-33cys}$ + CFA | 2.631 | 2.491 |

[a]Sera (1/100 dilution) from 2 control and 4 immunized mice 1 month after primary injection.

ELISA data presented in Table IV shows data from a bleed from our LPV-IGF$_{22-35}$ immunized mice (FIG. 6). The results in Table IV show that the mice gave a good response to that novel lipopeptide vaccine (LPV) formulation and are producing anti-IGF-1 antibodies. The antisera reacted both with the epitope peptide and with full-length human recombinant IGF-1 (Table IV).

TABLE IV

Serum Antibodies Present
in IGF$_{22-35}$ Lipopeptide Vaccinated Mice[a]

| Mouse Injected with: | ELISA READING (O.D. 450 nm) | |
|---|---|---|
| | IGF$_{22-33cys}$ Peptide | Recombinant IGF-1 |
| 1-No Vaccine | 0.577 | 0.487 |
| 2-No Vaccine | 0.611 | 0.647 |
| 3-No Vaccine | 0.664 | 0.693 |
| 4-LPV-IGF$_{22-35}$ | 3.022 | 1.387 |
| 5-LPV-IGF$_{22-35}$ | 2.904 | 1.986 |
| 6-LPV-IGF$_{22-35}$ | 1.539 | 1.327 |
| 7-LPV-IGF$_{22-35}$ | 1.711 | 1.544 |
| 8-LPV-IGF$_{22-35}$ | 2.540 | 1.119 |

[a]Sera taken from immunized mice 4 weeks following the primary injection, tested at a 1/100 dilution.

Figure 7:
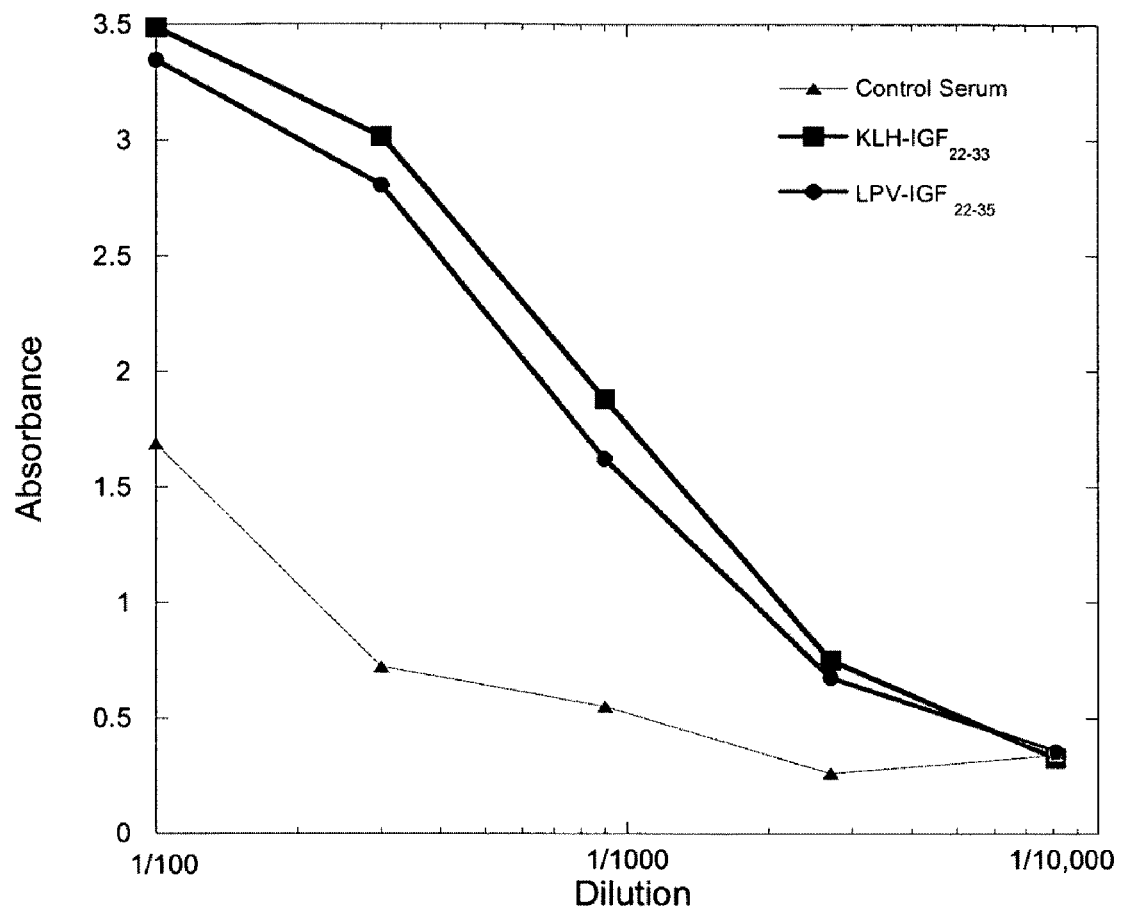
FIG. 7 shows an IGF-1 antisera titration.

An estimate of antibody titer can be obtained from the titration shown in FIG. 7. This titration compares antisera elicited by the LPV-IGF$_{22-35}$ vaccine administered in saline versus the KLH-IGF$_{22-33cys}$ vaccine which utilized complete Freund's adjuvant. The two vaccines display a virtually identical IGF-1 epitope and show similar activity by ELISA. We expect to see a rise in titer when the LPV-IGF$_{22-35}$ immunized mice are boosted. These results were quite unexpected, however, now we know that our lipopeptide vaccine will perform as well.

Essentially the same IGF epitope was used in this new lipopeptide vaccine as was previously attached to the KLH- and Qβ-based vaccines. All other criteria being equal, the self-adjuvanting IGF-1 lipopeptide formulation is equivalent to the KLH-based and Qβ-based vaccines for the present invention.

Measure the $^{125}$I-IGF-1 Binding Capacity

In an ELISA protocol sera must be diluted and the IGF-1 is then adsorbed onto a plate where it is immobilized. Therefore ELISA conditions do not closely represent the binding of an antibody to free, soluble IGF-1 as it occurs in undiluted blood. To mimic those circumstances we used a direct binding assay. A direct binding assay was devised using human recombinant $^{125}$I-IGF-1, undiluted whole serum, and immobilized Protein A Sepharose beads. This solid-phase separation system served to partition and to identify antibody-bound radioactive IGF-1 molecules. The assay provided a test for antibody activity in undiluted immune mouse serum versus control serum (Table V). This assay measured the IGF-1/antibody binding interaction under conditions (neat serum and soluble IGF-1) that mimic the in vivo situation encountered during therapeutic applications.

Mice were vaccinated with the KLH-IGF$_{22-33cys}$ antigen so that their sera could be compared to sera from non-immunized mice. The data show that antibody-bound $^{125}$I-IGF-1 is readily detected in whole immune serum. Similar results were obtained when the same sera and recombinant $^{125}$I-IGF-1 were incubated overnight to allow for an extended equilibration with the serum components. This indicates that the anti-IGF-1 antibodies can combine with the hormone in the presence of endogenous IGF-1, IGF-1 binding proteins and the other normal constituents of serum.

TABLE V

Reaction of Serum Antibodies with $^{125}$I-IGF-1[a]

| Mouse Injected with: | IGF-1 Bound (cpm) |
|---|---|
| 1-No Vaccine | 137 |
| 2-No Vaccine | 553 |
| 3-No Vaccine | 259 |
| 4-No Vaccine | 130 |
| 5-IGF-1 Vaccine | 1584 |
| 6-IGF-1 Vaccine | 4145 |
| 7-IGF-1 Vaccine | 1933 |
| 8-IGF-1 Vaccine | 4265 |

[a]Whole serum (10 μl) was incubated for 1 hour with $^{125}$I-IGF-1 and then Protein A beads were added to separate antibody-bound from free radioactive hormone.

Evaluate Insulin Cross-reactivity

Since the two hormone molecules have sequence similarities, cross-reaction of the anti-IGF-1 antibodies with insulin is a potential problem that must be addressed. Both an ELISA and $^{125}$I-insulin binding assay have been developed to evaluate this possible cross-reactivity of antibodies in sera from IGF-1 vaccinated mice.

Table VI shows results from the direct binding insulin assay. This assay utilized $^{125}$I-insulin (receptor grade {$^{125}$I}-Tyr$^{A14}$ porcine insulin) and the same Protein A Sepharose bead separation system used to measure the $^{125}$I-IGF-1/anti-IGF-1 interaction described above. In fact the data acquired for Table V and Table VI were part of the same simultaneously run experiment. Identical control and experimental anti-IGF$_{22-33cys}$ sera were used in both cases so the two sets of data can be directly compared. In sharp contrast to the clear, specific binding interaction displayed for IGF-1 (Table V), we found no difference between control and anti-IGF-1 sera when $^{125}$I-insulin was tested as an alternate ligand (Table VI).

TABLE VI

Reaction of Serum Antibodies with $^{125}$I-Insulin[a]

| Mouse Injected with: | Insulin Bound (cpm) |
|---|---|
| 1-No Vaccine | 431 |
| 2-No Vaccine | 992 |
| 3-No Vaccine | 311 |
| 4-No Vaccine | 1174 |
| 5-IGF-1 Vaccine | 159 |
| 6-IGF-1 Vaccine | 273 |
| 7-IGF-1 Vaccine | 284 |
| 8-IGF-1 Vaccine | 608 |

[a]Whole serum (10 μl) was incubated for 1 hour with $^{125}$I-Insulin and then Protein A beads were added to separate antibody-bound from free radioactive hormone.

These results indicate that any cross-reaction with insulin was minimal under conditions which mimic the in vivo situation. The findings further predict that no interference with the regulatory function of this hormone will be encountered during cancer prevention or longevity experiments in mice. The lack of insulin binding is consistent with the finding that these same IGF-1 immunized mice had blood glucose levels similar to non-immunized control animals (see Table II).

Block IGF-1 Bioactivity

Another aspect of the anti-IGF-1 immune response involves the effect that these vaccine-induced antibodies have on the bioactivity of IGF-1. When an antibody binds to IGF-1, the hormone should be sequestered and prevented from leaving the blood stream or reaching its target tissues. However, in addition, many of the epitope peptide vaccines of the instant invention are designed to elicit antibodies that will block the interaction of IGF-1 with its receptor or with its binding proteins. Blockage of such actions is easily detected since IGF-1 biochemical signaling pathways have been studied and its stimulatory effects are well defined.

IGF-1 bioactivity experiments using both serum-starved 3T3 cells (Siddals, K. W., et al., J Biol Chem 279:38353-38359 (2004)) and L6 myoblasts (Ballard, F. J., et al., Biochem J 233:223-230 (1986)) have been performed. Receptor-mediated stimulation of DNA and protein synthesis by IGF-1 has been measured in those cells by incorporation of $^3$H-thymidine and $^3$H-leucine, respectively. Next the ability of diluted control and anti-IGF-1 sera to block that receptor-mediated stimulation will be tested.

Akt is one of the early mediators in the signal transduction pathway initiated by the interaction of IGF-1 with its receptor (Zheng, W. H., and R. Quirion, BMC Neurosci 7:51 (2006)). Tests of the diluted control and anti-IGF-1 sera for blockade of IGF-1 mediated Akt activation may be performed. Vaccines that elicit antibodies which block the bioactivity of IGF-1 at the level of receptor binding would be highly regarded for use in subsequent longevity extension and cancer prevention studies.

Measure Downstream Signaling in Vaccinated Mice

Although the present invention is not limited in any way to any particular theory, it would be interesting to know if IGF-1 downstream signaling was affected by the IGF-1 vaccines of the present invention. To measure downstream signaling in vaccinated mice, test tissues from vaccinated versus control mice would be examined for reduced phospho-IGF-1-receptor levels using a commercially available specific antibody and western blot analysis. Receptor phosphorylation represents the earliest event in the IGF-1 signaling pathway. This approach will indicate that IGF-1 activity is impaired by vaccination.

The protocol supplied with the anti-phospho-IGF-1-receptor antibody is explicit with regard to the needed solutions and reagents, sample preparation, PAGE, the protein blotting procedures, antibody incubations and the detection and quantitation of the phospho-IGF-1-receptor.

Longevity and Cancer Prevention Studies in Mouse Model Systems

Select Candidate IGF-1 Vaccines

One or two of the IGF-1 epitope vaccines will be chosen for further study based upon immunization criteria such as safety, antibody titer, specificity, IGF-1 binding capacity, bioactivity blockade and minimal cross-reactivity with insulin. Presently the highly characterized KLH-IGF$_{22-33cys}$ and LPV-IGF$_{22-35}$ formulations meet those criteria extraordinarily well. The KLH-IGF$_{22-33cys}$ vaccine was subjected to testing in a mouse longevity model and cancer prevention model to exemplify the effectiveness of a vaccine to the [IGF$_{22-35cys}$] epitope.

Based on the effectiveness of the IFG$_{22-33cys}$ formulations in the assays presented above, data is considered compatible for both the KLH-IGF$_{22-33cys}$ and LPV-IGF$_{22-35}$ formulations. Continued evaluations will be made, especially of the Qβ-based antigens, to determine if even more potent vaccines will arise. Qβ-based antigen formulations hold the potential for providing even more potent IGF-1 vaccines. Using vaccine cocktails containing two or more epitope antigens of the present invention is also envisioned (i.e., simultaneously) as well as vaccinating with two or more epitope antigens of the present invention sequentially.

Actively Immunize Mice for Longevity Studies

In-house longevity testing of the KLH-based, Qβ-based and LPV-based IGF-1 vaccines are performed by vaccinating subject mice and following published guidelines for performing meaningful longevity research in mice (Miller, R. A., and N. L. Nadon, et al. J Gerontol A Biol Sci Med Sci 55:B117-123 (2000); Nadon, N. L. et al., J Gerontol A Biol Sci Med Sci 61:813-815 (2006); Nadon, N. L., et al. Aging cell 5:9-15 (2006); Warner, H. R., et al. Mech Ageing Dev 115:199-207 (2000)). Particular attention will be paid to the genetic background of the specific pathogen-free mice as well as their housing and diet.

A Phase I survival analysis is conducted using 100 CB6F1×C3D2F1 (or CB6F1) mice immunized with the selected IGF-1 vaccines and 100 control mice immunized with the corresponding carrier alone. Specific pathogen-free mice are used and the testing protocol provides sufficient statistical power to detect lifespan increases in the 10-15 percent range. Simultaneously treated mice not enrolled in the longevity study are assessed to determine if IGF-1 vaccination is having its expected effects. Mice are non-invasively monitored for several age-sensitive traits, such as weight gain, cataract development, cognitive abilities and spontaneous activity.

Actively Immunize Mice for Cancer Prevention Studies

Testing of the KLH-IGF$_{22-33cys}$ vaccine using C57BL/6J Tg(WapTAg) 1Knw spontaneous tumor mice (FIG. 5) has begun. These vaccinated mice were healthy and growing normally at 5 months old.

The transgenic TRAMP prostate cancer mouse model has been shown to respond to genetic alternations in the GH-IGF-1 axis, which resulted in greatly improved survival (Majeed, N., et al., Oncogene 24:4736-4740 (2005)). At the 35-week time point 74% of control mice had already died but only 18% of the genetically IGF-1 depressed mice had succumbed. TRAMP mice are commercially available so that this system will also be used to test our IGF-1 vaccines for providing a survival effect similar to that bestowed by genetic manipulation.

A third spontaneous cancer model uses p53 tumor suppressor knockout mice. These p53$^{-/-}$ animals succumb to cancer at 104 days of age but calorie restriction improves their survival to 169 days, a 63% delay in tumor mortality (Hursting, S. D., et al., Cancer Res 57:2843-2846 (1997)). Another calorie restriction model used p53$^{+/-}$ mice to establish a survival connection to suppressed IGF-1 levels ( Dunn, S. E., et al., Cancer Res 57:4667-4672 (1997)). Homozygous and heterozygous p53 deficient mice are both commercially available.

AKR mice are a forth strain that is suitable for testing since they are widely used in cancer research for their high cancer incidence and relatively short lifespan. A spontaneous thymic lymphoma develops in approximately 90% of the mice between 7 and 12 months of age (Gross, L. 1970. Oncogenic viruses. Pergamon Press, Ltd., Oxford).

Lastly, the BK5.IGF-1 transgenic strain (DiGiovanni, J., et al., Proc Natl Acad Sci U S A 97:3455-3460 (2000)) is considered for the IGF-1 vaccine research. These mice constitutively express human IGF-1, which causes spontaneous tumorigenesis in their prostate epithelium.

Monitor Mice for Tumor Development

Soft tissue sarcomas appear and grow rapidly in C57BL/6J Tg(WapTAg) 1Knw mice (Husler, M. R., et al., Transgenic Res 7:253-263 (1998)). Thus both the IGF vaccinated and control KLH vaccinated groups are being monitored to determine if there is any delay in the appearance of visible tumors and/or prolonged survival time for the IGF-1 vaccinated mice.

For longevity studies and for survival studies using the different cancer models, each mouse is observed until its natural death or until it becomes ill. Survival curves are constructed using the Kaplan-Meier method and intergroup differences were evaluated using the log-rank test.

Influence of IGF-1 Vaccination on Carcinogenesis

As mentioned above in the Detailed Description of the Invention, the rationale for lowering IGF-1 levels applies both to prolonging lifespan and to inhibiting carcinogenesis. The same dietary restriction and mutational perturbations of IGF-1 signaling which increase longevity can also delay the development of cancer. Thus, a pilot experiment was initiated to test the effects of IGF-1 vaccination on mice that are prone to tumor development by virtue of their SV40 Tag transgene expression (Husler, M. R., et al., Transgenic Res 7:253-263.6, 1998). The result of this ongoing experiment is highly pertinent to the proposed longevity studies since it shows that our IGF-1 vaccine can delay the onset of carcinogenesis. This outcome would demonstrate that the specifically induced antibodies are, in fact, modulating IGF-1 activity in those live animals. As IGF-1 vaccination inhibits carcinogenesis as shown herein, this is supportive of IGF-1 vaccination providing similar delaying effects on an array of diseases and age-dependent deterioration and thus should prolong lifespan.

Briefly, 12 virgin female C57BL/6J Tg(WapTAg) 1Knw spontaneous tumor mice (Husler, M. R., et al., Transgenic Res 7:253-263.6, 1998) having the same date of birth were used. When 41 days old, 6 mice were immunized with the KLH-IGF$_{22-33cys}$ vaccine and 6 with the KLH control vaccine, as previously described above, to exemplify the ability of the IGF-1 vaccines of the present invention to delay and/or prevent tumor formation and growth. Subsequent booster injections were given when they were 70 and 272 days old. The early growth pattern of these same control and experimental C57BL/6J Tg(WapTAg) 1Knw mice was shown in FIG. 5.

Figure 8:
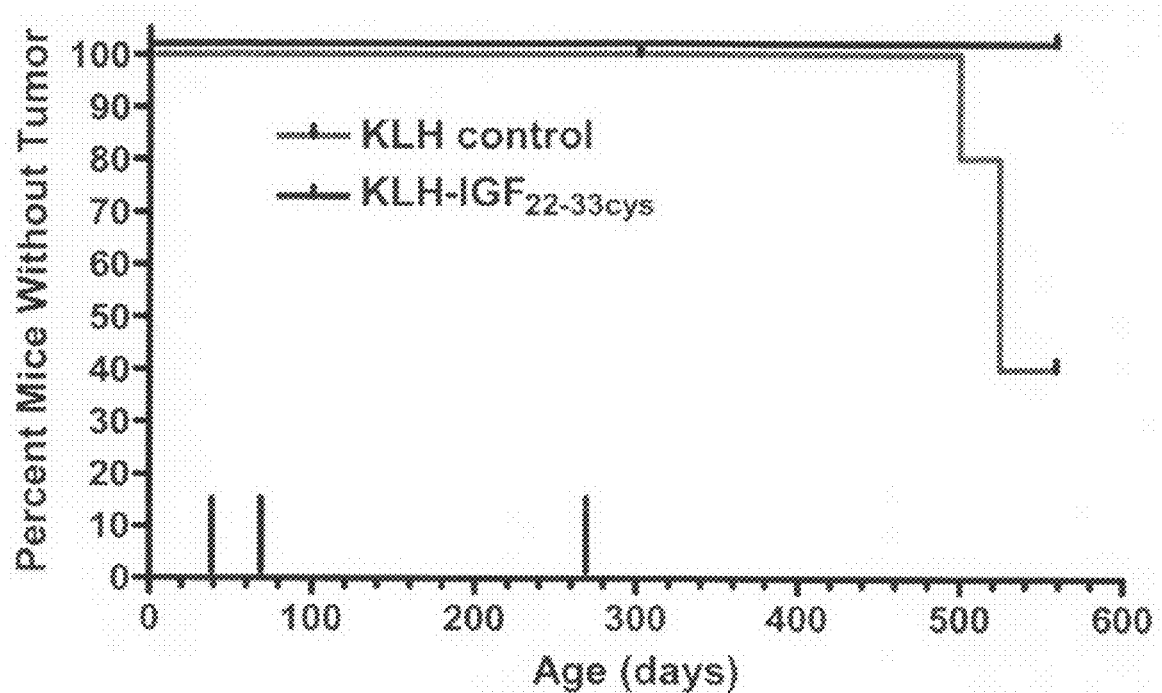
FIG. 8(a) shows tumors in KLH immunized control mice (6) versus KLH-IGF$_{22-33cys}$ immunized mice (6); Arrows Denote Vaccination.
FIG. 8(b) shows one representative KLH immunized positive control mouse with a tumor.
Figure 8:
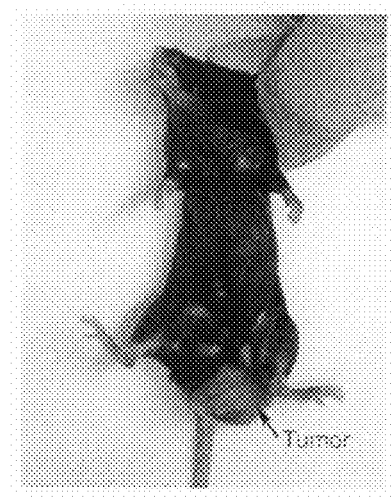

One of the 6 control mice had to be scarified due to a cage accident when it was 302 days old and thus was censored in the data set shown in FIG. 8a. Recently, 3 of the remaining 5 control mice were sacrificed because each had gradually developed a clearly visible severe mass in the uterus ~1 cm in diameter (see, FIG. 8b) which was histologically classified as a high-grade cervical sarcoma. The 2 remaining control mice and all 6 of the KLH-IGF$_{22-33cys}$ vaccinated mice appear healthy, apparently tumor-free and they will continue to be monitored. The comprehensive Prism biostatistics program (Graph Pad Software, San Diego, Calif.) was used to analyze and plot this data following the method of Kaplan and Meier (FIG. 8a). A comparison of the curves by the log-rank test showed that they are significantly different with a one-tailed P value=0.0168 thereby demonstrating the effectiveness of the IGF-1 vaccines of the present invention in the delay and/or prevention of tumor formation and growth.

Tumor development, thus far, has been prevented in the KLH-IGF$_{22-33cys}$ immunized mice but not in the KLH immunized mice. This cancer preventive action implies that the specifically induced antibodies are, in fact, selectively suppressing IGF-1 activity in those live animals. Therefore, the results of this pre-clinical trial support the underlying rationale of both therapeutic applications. Namely, that IGF-1 immunization can be used to specifically reduce the action of that hormone and that this intervention should concomitantly lower the incidence of cancer and prolong lifespan. Indeed, genetic analyses indicate that the same cellular changes leading to longevity preferentially antagonize tumor cell growth, thereby linking these two processes mechanistically. (Pinkston, J. M., et al., 2006, Science 313:971-975; Pinkston-Gosse, J., and C. Kenyon. 2007. Nat Genet 39:1403-1409; Greer, E. L., and A. Brunet. 2005, Oncogene 24:7410-7425). Since carcinogenesis can be impeded by the specific antibody-mediated modulation of IGF-1 activity, there is good reason to anticipate that this same intervention should also improve the general health and longevity of animals.

Animal Safety Information

Mutational alterations of the IGF-1 pathway often affect the organism prematurely and can, for example, produce a high level of neonatal lethality and dwarf mice (Kenyon, C. Cell 120:449-460 (2005); Lupu, F., et al., Dev Biol 229:141-162 (2001); Holzenberger, supra). Anti-IGF-1 antibody treatment can prevent such problems if begun by vaccination in early adult life when IGF-1 is no longer needed for growth (Kenyon, C. Cell 120:449-460 (2005); Lupu, F., et al., Dev Biol 229:141-162 (2001); Yakar, supra) or vital functions. Thus, immunotherapy blocks IGF-1 receptor-mediated signaling in a safe and more controllable manner.

The initial immunization of mice with Complete Freund's Adjuvant may produce a transient, small decrease in weight but the animals recover within one week (Hu, J G, et al., Chem Pharm Bull (Tokyo) 37:3042-3046 (1989)). Alternative adjuvants could be used but there is no assurance that an equally vigorous immune response will be achieved. However, the self-adjuventing vaccines of the present invention have been shown herein to generate an equally vigorous immune response (FIG. 7). Booster vaccinations have the potential to elicit anaphylactic shock, however, this is a rare occurrence and was not seen in the mice that were immunized and boosted with the IGF-1 vaccine. Intraperitoneal injections should be performed by an experienced individual using a short, ½-inch, 27 gauge needle so that the mouse is not harmed.

Blockage of IGF-1 activity could conceivably produce an adverse effect in the mice. However this problem is unlikely when treatment is started after the greater part of their growth has ended. Moreover normal growth and development has been observed when hepatic IGF-1 production (75% of total) was selectively ablated in mice (Yakar, S, et al., Proc Natl Acad Sci USA 96:7324-7329 (1999)). No short-term problems have been observed in the numerous mice that were immunized and boosted with the IGF-1 vaccine.

What is claimed is:

1. A method for reducing or delaying tumor growth in an adult treated human as compared to an untreated human, the method comprising:

a) providing one or more antigens, the antigen(s) characterized by the ability to stimulate the production of circulating antibodies which specifically bind to human IGF-1 when administered to a human under conditions appropriate for the stimulation of an immune response and wherein said antigen is selected from one or more of LPV-IGF1-16, LPV-IGF22-35, LPV-IGF29-42, LPV-IGF56-70, KLH-IGF28-41, KLH-IGF22-33, KLH-IGF30-38, KLH-IGF29-42, KLH-IGF22-35, KLH-IGF1-6, KLH-IGF61-70, KLH-IGF1-16, KLH-IGF56-70, KLH-IGF30-38, KLH-IGF61-70, KLH-IGF29-42, KLH-IGF56-70, Qβ-IGF28-41, Qβ-IGF22-33, Qβ-IGF30-38, Qβ-IGF29-42, Qβ-IGF22-35, Qβ-IGF1-6, Qβ-IGF61-70, Qβ-IGF1-16, Qβ-IGF56-70, Qβ-IGF30-38, Qβ-IGF61-70, Qβ-IGF29-42 and Qβ-IGF56-70;

b) administering the antigen to said human to create a treated human under conditions appropriate for the stimulation of an immune response, thereby stimulating the production of circulating antibodies which specifically bind to human IGF-1; and c) correlating the administration of the antigen to said treated human with a reduction in growth of one or more tumors.

2. The method of claim 1, wherein said untreated human is represented by historic data.

3. The method of claim 1, wherein said reduction in tumor growth is accompanied by a decrease in tumor size.

4. The method of claim 1, wherein the antigen is encoded in a nucleotide sequence and said nucleotide sequence is administered to said adult human.

5. the method of claim 1, wherein said antigen is selected from one or more of LPV-IGF22-35, KLH-IGF22-35 and Qβ-IGF22-35.

6. The method of claim 1, wherein said antigen is selected from one or more of LPV-IGF1, LPV-IGF22-35, LPV-IGF29-42 and LPV-IGF56-70.

7. The method of claim 1, wherein said antigen is selected from one or more of KLH-IGF28-41, KLH-IGF22-33, KLH-IGF30-38, KLH-IGF29-42, KLH-IGF22-35, KLH-IGF1-6, KLH-IGF61-70, KLH-IGF1-16, KLH-IGF56-70, KLH-IGF30-38, KLH-IGF61-70, KLH-IGF29-42, KLH-IGF56-70.

8. then method of claim 1, wherein said antigen is selected from one or more of Qβ-IGF28-41, Qβ-IGF22-33, Qβ-IGF30-38, Qβ-IGF29-42, Qβ-IGF22-35, Qβ-IGF1-6, Qβ-IGF61-70, Qβ-IGF1-16, Qβ-IGF56-70, Qβ-IGF30-38, Qβ-IGF61-70, Qβ-IGF29-42 and Qβ-IGF56-70.

* * * * *

SEQUENCE LISTING

<160> NUMBER OF SEQ ID NOS: 3

<210> SEQ ID NO 1
<211> LENGTH: 70
<212> TYPE: PRT
<213> ORGANISM: Homo sapiens

<400> SEQUENCE: 1

Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
    50                  55                  60

Lys Pro Ala Lys Ser Ala
65                  70

<210> SEQ ID NO 2
<211> LENGTH: 70
<212> TYPE: PRT
<213> ORGANISM: Homo sapiens

<400> SEQUENCE: 2

Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
    50                  55                  60

Lys Pro Ala Lys Ser Ala
65                  70

<210> SEQ ID NO 3
<211> LENGTH: 69
<212> TYPE: PRT
<213> ORGANISM: Mus sp.

<400> SEQUENCE: 3

Gly Pro Glu Thr Leu Cys Gly Ala Glu Leu Val Asp Ala Leu Gln Phe
 1               5                  10                  15

Val Cys Gly Pro Arg Gly Phe Tyr Phe Asn Lys Pro Thr Gly Tyr Gly
                20                  25                  30

Ser Ser Arg Arg Ala Pro Gln Thr Gly Ile Val Asp Glu Cys Cys Phe
            35                  40                  45

Arg Ser Cys Asp Leu Arg Arg Leu Glu Met Tyr Cys Ala Pro Leu Lys
    50                  55                  60

Pro Thr Lys Ala Ala
65